United States Patent
Bedingham et al.

(10) Patent No.: US 6,734,401 B2
(45) Date of Patent: May 11, 2004

(54) ENHANCED SAMPLE PROCESSING DEVICES, SYSTEMS AND METHODS

(75) Inventors: William Bedingham, Woodbury, MN (US); Raj Rajagopal, Woodbury, MN (US); Barry W. Robole, Woodville, WI (US); Kannan Seshadri, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 168 days.

(21) Appl. No.: 09/894,810

(22) Filed: Jun. 28, 2001

(65) Prior Publication Data

US 2002/0047003 A1 Apr. 25, 2002

Related U.S. Application Data

(60) Provisional application No. 60/214,508, filed on Jun. 28, 2000, provisional application No. 60/214,642, filed on Jun. 28, 2000, provisional application No. 60/237,072, filed on Oct. 2, 2000, provisional application No. 60/260,063, filed on Jan. 6, 2001, and provisional application No. 60/284,637, filed on Apr. 18, 2001.

(51) Int. Cl.[7] .............................. F27B 9/16; F27B 9/36; G01N 1/18; C12Q 1/34
(52) U.S. Cl. ...................... 219/388; 219/652; 219/628; 435/288.4
(58) Field of Search .................... 219/388, 618, 219/627–629, 630, 652, 667; 435/288.4; 62/3.2, 3.3; 422/105, 186, 187, 285, 307, 308; 436/180

(56) References Cited

U.S. PATENT DOCUMENTS

| | | | |
|---|---|---|---|
| 3,555,284 A | 1/1971 | Anderson | |
| 3,795,451 A | 3/1974 | Mailen | |
| 3,798,459 A | 3/1974 | Anderson et al. | |
| 3,873,217 A | 3/1975 | Anderson et al. | |
| 4,030,834 A | * 6/1977 | Bauer et al. | .................. 422/72 |
| 4,244,916 A | 1/1981 | Guigan | ....................... 422/72 |
| 5,049,591 A | 9/1991 | Hayashi et al. | |
| 5,128,197 A | 7/1992 | Kobayashi et al. | |
| 5,135,786 A | 8/1992 | Hayashi et al. | |
| 5,139,832 A | 8/1992 | Hayashi et al. | |

(List continued on next page.)

FOREIGN PATENT DOCUMENTS

| | | | |
|---|---|---|---|
| DE | 37 12 624 A1 | 11/1988 | ........... B04B/15/02 |
| EP | 0 169 306 | 1/1986 | |
| EP | 0 693 560 A2 | 1/1996 | |
| EP | 807468 | * 11/1997 | |
| EP | 0 810 030 A1 | 12/1997 | ............. B01L/7/00 |
| WO | WO 94/29400 | 12/1994 | |
| WO | WO 95/18676 | 7/1995 | |
| WO | WO 96/34028 | 10/1996 | |
| WO | WO 96/34029 | 10/1996 | |
| WO | WO 96/35458 | 11/1996 | |

(List continued on next page.)

OTHER PUBLICATIONS

*Handbook of Pressure Sensitive Adhesive Technology*, Donatas Satas (Ed.) 2nd Edition, p. 172, and FIG. 8–16 on p. 173, Van Nostrand Reinhold, New York, NY, 1989.

(List continued on next page.)

*Primary Examiner*—Joseph Pelham
(74) *Attorney, Agent, or Firm*—Christopher D. Gram; Robert W. Sprague

(57) ABSTRACT

Devices, systems, and methods for processing sample materials. The sample materials may be located in a plurality of process chambers in the device, which is rotated during heating of the sample materials.

112 Claims, 22 Drawing Sheets

U.S. PATENT DOCUMENTS

| | | | |
|---|---|---|---|
| 5,145,935 A | | 9/1992 | Hayashi |
| 5,278,377 A | | 1/1994 | Tsai |
| 5,429,810 A | * | 7/1995 | Knaepler et al. ............ 422/307 |
| 5,446,270 A | | 8/1995 | Chamberlain et al. |
| 5,461,134 A | | 10/1995 | Leir et al. |
| 5,496,520 A | * | 3/1996 | Kelton et al. .................. 422/64 |
| 5,529,708 A | | 6/1996 | Palmgren et al. |
| 5,639,428 A | * | 6/1997 | Cottingham ................. 422/105 |
| 5,720,923 A | * | 2/1998 | Haff et al. ................ 435/287.3 |
| 5,721,123 A | | 2/1998 | Hayes et al. |
| 5,819,842 A | * | 10/1998 | Potter et al. .................... 62/3.2 |
| 5,863,502 A | | 1/1999 | Southgate et al. ............. 422/58 |
| 5,925,455 A | | 7/1999 | Bruzzone et al. |
| 6,007,914 A | | 12/1999 | Joseph et al. |
| 6,013,513 A | | 1/2000 | Reber et al. |
| 6,030,581 A | | 2/2000 | Virtanen |
| 6,063,589 A | | 5/2000 | Kellogg et al. |
| 6,093,370 A | * | 7/2000 | Yasuda et al. ............ 435/288.4 |
| 6,143,248 A | | 11/2000 | Kellogg et al. |
| 6,319,469 B1 | | 11/2001 | Mian et al. |
| 6,467,275 B1 | * | 10/2002 | Ghoshal ....................... 62/3.3 |
| 6,527,432 B2 | * | 3/2003 | Kellogg et al. ............. 422/100 |
| 6,558,947 B1 | * | 5/2003 | Lund et al. .............. 435/288.4 |
| 6,572,830 B1 | * | 6/2003 | Burdon et al. .............. 422/186 |
| 6,660,147 B1 | | 12/2003 | Woudenberg et al. |

FOREIGN PATENT DOCUMENTS

| | | | |
|---|---|---|---|
| WO | WO 96/41864 | 12/1996 | |
| WO | WO 97/21090 | 6/1997 | |
| WO | WO 97/46707 | 12/1997 | ............ C12Q/1/68 |
| WO | WO 98/07019 | 2/1998 | |
| WO | WO 98/49340 | 11/1998 | |
| WO | 9850147 | * 11/1998 | |
| WO | WO 98/53311 | 11/1998 | .......... G01N/33/00 |
| WO | WO 99/09394 | 2/1999 | |
| WO | WO 99/55827 | 11/1999 | |
| WO | WO 99/58245 | 11/1999 | |
| WO | WO 99/67639 | 12/1999 | |
| WO | WO 00/05582 | 2/2000 | |
| WO | WO 00/40750 | 7/2000 | |
| WO | WO 00/50172 | 8/2000 | |
| WO | WO 00/50642 | 8/2000 | |
| WO | WO 00/68336 | 11/2000 | |
| WO | WO 00/69560 | 11/2000 | |
| WO | WO 00/78455 | 12/2000 | |
| WO | WO 00/79285 | 12/2000 | |

OTHER PUBLICATIONS

*Handbook of Pressure Sensitive Adhesive Technology*, $3^{rd}$ Edition, p. 508–517.

*Test Methods for Pressure Sensitive Adhesive Tapes*, Pressure Sensitive Tape Council, (1996).

* cited by examiner

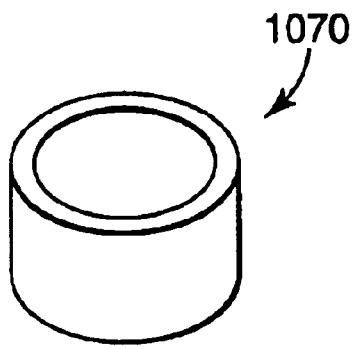
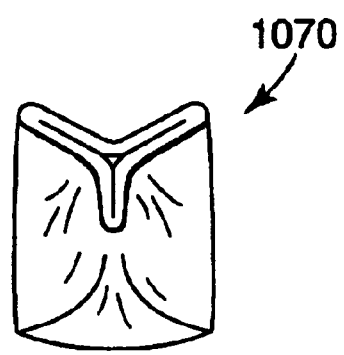
Fig. 23A  Fig. 23B
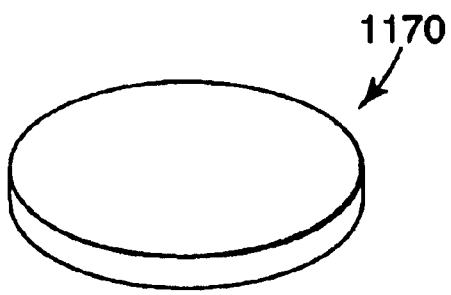
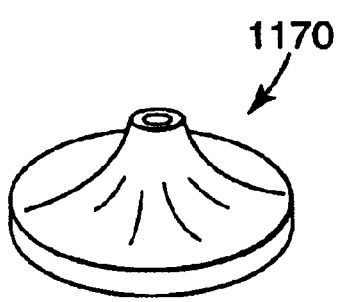
Fig. 24A  Fig. 24B

US 6,734,401 B2

ENHANCED SAMPLE PROCESSING DEVICES, SYSTEMS AND METHODS

RELATED APPLICATIONS

This application claims the benefit of U.S. Provisional Patent Application Serial No. 60/214,508 filed on Jun. 28, 2000 and titled THERMAL PROCESSING DEVICES AND METHODS; U.S. Provisional Patent Application Serial No. 60/214,642 filed on Jun. 28, 2000 and titled SAMPLE PROCESSING DEVICES, SYSTEMS AND METHODS; U.S. Provisional Patent Application Serial No. 60/237,072 filed on Oct. 2, 2000 and titled SAMPLE PROCESSING DEVICES, SYSTEMS AND METHODS; U.S. Provisional Patent Application Serial No. 60/260,063 filed on Jan. 6, 2001 and titled SAMPLE PROCESSING DEVICES, SYSTEMS AND METHODS; and U.S. Provisional Patent Application Serial No. 60/284,637 filed on Apr. 18, 2001 and titled ENHANCED SAMPLE PROCESSING DEVICES, SYSTEMS AND METHODS—all of which are hereby incorporated by reference in their entireties.

GRANT INFORMATION

The present invention may have been made with support from the U.S. Government under NIST Grant No. 70NANB8H4002. The U.S. Government may have certain rights in the inventions recited herein.

TECHNICAL FIELD

The present invention relates to devices, methods and systems for processing of sample materials, such as methods used to amplify genetic materials, etc.

BACKGROUND

Many different chemical, biochemical, and other reactions are sensitive to temperature variations. Examples of thermal processes in the area of genetic amplification include, but are not limited to, Polymerase Chain Reaction (PCR), Sanger sequencing, etc. The reactions may be enhanced or inhibited based on the temperatures of the materials involved. Although it may be possible to process samples individually and obtain accurate sample-to-sample results, individual processing can be time-consuming and expensive.

One approach to reducing the time and cost of thermally processing multiple samples is to use a device including multiple chambers in which different portions of one sample or different samples can be processed simultaneously. When multiple reactions are performed in different chambers, however, one significant problem can be accurate control of chamber-to-chamber temperature uniformity. Temperature variations between chambers may result in misleading or inaccurate results. In some reactions, for example, it may be critical to control chamber-to-chamber temperatures within the range of ±1° C. or less to obtain accurate results.

The need for accurate temperature control may manifest itself as the need to maintain a desired temperature in each of the chambers, or it may involve a change in temperature, e.g., raising or lowering the temperature in each of the chambers to a desired setpoint. In reactions involving a change in temperature, the speed or rate at which the temperature changes in each of the chambers may also pose a problem. For example, slow temperature transitions may be problematic if unwanted side reactions occur at intermediate temperatures. Alternatively, temperature transitions that are too rapid may cause other problems. As a result, another problem that may be encountered is comparable chamber-to-chamber temperature transition rate.

In addition to chamber-to-chamber temperature uniformity and comparable chamber-to-chamber temperature transition rate, another problem may be encountered in those reactions in which thermal cycling is required is overall speed of the entire process. For example, multiple transitions between upper and lower temperatures may be required. Alternatively, a variety of transitions (upward and/or downward) between three or more desired temperatures may be required. In some reactions, e.g., polymerase chain reaction (PCR), thermal cycling must be repeated up to thirty or more times. Thermal cycling devices and methods that attempt to address the problems of chamber-to-chamber temperature uniformity and comparable chamber-to-chamber temperature transition rates, however, typically suffer from a lack of overall speed—resulting in extended processing times that ultimately raise the cost of the procedures.

One or more of the above problems may be implicated in a variety of chemical, biochemical and other processes. Examples of some reactions that may require accurate chamber-to-chamber temperature control, comparable temperature transition rates, and/or rapid transitions between temperatures include, e.g., the manipulation of nucleic acid samples to assist in the deciphering of the genetic code. See, e.g., T. Maniatis et al. *Molecular Cloning, A Laboratory Manual*, Cold Spring Harbor Laboratory (1982). Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

One common example of a reaction in which all of the problems discussed above may be implicated is PCR amplification. Traditional thermal cycling equipment for conducting PCR uses polymeric microcuvettes that are individually inserted into bores in a metal block. The sample temperatures are then cycled between low and high temperatures, e.g., 55° C. and 95° C. for PCR processes. When using the traditional equipment according to the traditional methods, the high thermal mass of the thermal cycling equipment (which typically includes the metal block and a heated cover block) and the relatively low thermal conductivity of the polymeric materials used for the microcuvettes result in processes that can require two, three, or more hours to complete for a typical PCR amplification.

One attempt at addressing the relatively long thermal cycling times in PCR amplification involves the use of a device integrating 96 microwells and distribution channels on a single polymeric card. Integrating 96 microwells in a single card does address the issues related to individually loading each sample cuvette into the thermal block. This approach does not, however, address the thermal cycling issues such as the high thermal mass of the metal block and heated cover or the relatively low thermal conductivity of the polymeric materials used to form the card. In addition, the thermal mass of the integrating card structure can extend thermal cycling times. Another potential problem of this approach is that if the card containing the sample wells is not seated precisely on the metal block, uneven well-to-well temperatures can be experienced, causing inaccurate test results.

Yet another problem that may be experienced in many of these approaches is that the volume of sample material may be limited and/or the cost of the reagents to be used in connection with the sample materials may also be limited and/or expensive. As a result, there is a desire to use small volumes of sample materials and associated reagents. When using small volumes of these materials, however, additional problems related to the loss of sample material and/or reagent volume through vaporization, etc. may be experienced as the sample materials are, e.g., thermally cycled.

Another problem experienced in the preparation of finished samples (e.g., isolated or purified samples of, e.g., nucleic acid materials such as DNA, RNA, etc.) of human, animal, plant, or bacterial origin from raw sample materials (e.g., blood, tissue, etc.) is the number of thermal processing steps and other methods that must be performed to obtain the desired end product (e.g., purified nucleic acid materials). In some cases, a number of different thermal processes must be performed, in addition to filtering and other process steps, to obtain the desired finished samples. In addition to suffering from the thermal control problems discussed above, all or some of these processes may require the attention of highly skilled professionals and/or expensive equipment. In addition, the time required to complete all of the different process steps may be days or weeks depending on the availability of personnel and/or equipment.

One example is in the preparation of a finished sample (e.g., purified nucleic acid materials) from a starting sample (e.g., a raw sample such as blood, bacterial lysate, etc.). To obtain a purified sample of the desired materials in high concentrations, the starting sample must be prepared for, e.g., PCR, after which the PCR process is performed to obtain a desired common PCR reaction product. The common PCR reaction product must then be prepared for, e.g., Sanger sequencing, followed by performance of the Sanger sequencing process. Afterwards, the multiplexed Sanger sequencing product must be demultiplexed. After demultiplexing, the finished Sanger sequencing product is ready for further processing. This sequence of events may, however, have occurred over days or even weeks. In addition, the technical nature of the processes requires highly skilled personnel to obtain accurate results.

Approaches at using disc-based devices to integrate various thermal processing steps into a single device suffer from a number of disadvantages including the use of high cost silicon substrates and the incorporation of high cost heating and/or cooling systems built into the discs. As a result, the cost of the discs can be prohibitive to their widespread use. See, e.g., International Publication Nos. WO 98/07019 (Kellog et al.); WO 99/09394 (Hubbard et al.).

SUMMARY OF THE INVENTION

The present invention provides devices, systems, and methods for processing sample materials. The sample materials may be located in a plurality of process chambers in the device, which is rotated during heating of the sample materials. The rotation may provide a variety of advantages over known sample processing methods, systems, and devices.

One advantage of rotating the device during heating of the sample material in the process chambers is that, as the temperature of the sample materials rises and vapor is formed, it typically attempts to move upstream, i.e., towards the axis of rotation of the device. However, once outside of the process chambers, the vaporized materials tend to condense as they cool. The condensed sample materials are returned to the sample chambers due to the centrifugal forces provided by the rotation. As a result, rotation during heating helps to retain the sample materials in the process chambers during heating—an advantage that may be particularly significant where small volumes of sample materials and/or reagents are used.

Another advantage may include, e.g., enhanced cooling through convection as the device rotates during processing. As a result, the cooling of sample materials may be expedited without relying solely on more complex systems that include, e.g., Peltier elements, etc. to provide for the removal of thermal energy from the sample materials.

Another potential advantage of rotating the device while heating the sample material is that control over heating of sample materials in the process chambers may be enhanced. For example, increasing the rotational speed of the device may improve heating control by essentially damping the temperature increase of the sample material (by, e.g., increasing convective cooling during the heating process). Changing the rotational speed of the device may also be used to, e.g., control the amount of energy reaching each of the process chambers.

Another potential advantage is that uniformity of sample material temperature in the different process chambers may also be improved by rotating the device during heating. For example, where heating is accomplished by directing electromagnetic energy at thermal structures in a base plate on which the device is rotating, rotation can be helpful to, e.g., prevent uneven heating due to hot spots generated by the electromagnetic energy source.

Other advantages of the devices and methods of the present invention include the ability to perform complex thermal processing on sample materials in a manner that reduces variability of the results due to, e.g., human error. Further, with respect to the processing of biological materials for, e.g., genetic amplification, this advantage may be achieved by operators that have a relatively low skill level as compared to the higher skill level of operators required to perform currently used methods.

As discussed above, the thermal control advantages of the devices, methods and systems of the present invention may include chamber-to-chamber temperature uniformity, comparable chamber-to-chamber temperature transition rates, and the increased speed at which thermal energy can be added or removed from the process chambers. Among the device features that can contribute to these thermal control advantages are the inclusion of a reflective layer (e.g., metallic) in the device, baffle structures to assist in removing thermal energy from the device, and low thermal mass of the device. By including thermal indicators and/or absorbers in the devices, enhanced control over chamber temperature may be achieved even as the device is rotated during processing.

In those embodiments that include connected process chambers in which different processes may be sequentially performed on a starting sample, the present invention may provide an integrated solution to the need for obtaining a desired finished product from a starting sample even though multiple thermal processes are required to obtain the finished product.

In other embodiments in which the process chambers are multiplexed from a loading chamber (in which the starting sample is loaded), it may be possible to obtain multiple finished samples from a single starting sample. Those multiple finished samples may be the same materials where the multiplexed process chambers are designed to provide the same finished samples. Alternatively, the multiple finished samples may be different samples that are obtained from a single starting sample.

For those embodiments of the devices that include distribution channels formed in a metallic layer, the ductility of the metallic layer may provide a further advantage in that it may be possible to close or crush selected distribution channels to tailor the devices for specific test protocols, adjust for smaller sample material volumes, etc. It may also be advantageous to isolate the process chambers by closing or crushing the distribution channels after distributing sample materials to the process chambers.

For those embodiments that include a reflective layer forming a portion of each of the desired process chambers, the present invention may also provide the advantage of improved signal strength when the samples contained in the process chambers are monitored for fluorescent or other electromagnetic energy signals. The signal strength may be improved if the reflective (e.g., metallic) layer reflects the electromagnetic energy being monitored as opposed to absorbing the energy or allowing it to be transmitted away from a detector. The signal strength may be even further improved if the metallic layer is formed into a shape that acts as a focusing reflector (e.g., parabolic reflector). If electromagnetic energy used to interrogate and/or heat materials in the process chambers is reflected by the reflective layer, then that layer may also improve the efficiency of the interrogation and/heating processes by effectively doubling the path length of the electromagnetic energy through the sample materials in the process chambers.

A further advantage of the embodiments of the invention that include a metallic layer is the relatively high strength to thickness ratio provided by the metallic layer. This may be particularly true when compared to devices that rely solely on polymeric materials to construct thermal processing devices. In addition to physical strength, the metallic layer may also provide beneficial barrier properties, i.e., a resistance to moisture vapor permeability. Another advantage that may also be provided by a metallic layer is its amenability to piercing without fracture to either introduce materials into, e.g., a loading chamber, or to remove materials, e.g., a finished sample, from a process chamber.

An advantage of those embodiments including filter chambers with capture plugs is that filtering material appropriate for the particular process being performed may be added at the point-of-use. For example, if the device is being used for genetic amplification, a filtering material designed to allow passage of nucleic acid materials of particular sizes may be delivered to the filter chamber before processing of the genetic materials.

Advantages of those embodiments including the valving mechanisms of the present invention include the ability to control movement of materials through the array of chambers and passageways present on the devices. A further advantage of the preferred valving mechanisms is that they do not contaminate the sample materials (as may, e.g., wax valves). Another advantage of the valving mechanisms may include the ability to selectively open the valves using, e.g., laser energy, while the devices are rotating during sample processing.

Advantages of those embodiments of the invention that include control patterns include the ability to control the delivery of electromagnetic energy to the device or other functions, e.g., detection of changes in the process chambers, without requiring changes to the hardware and/or software used in the system employing the device. For example, the amount and/or wavelength of electromagnetic energy delivered to the process chambers and/or valves can be controlled using a control pattern on the device. Such control may further reduce the operator error associated with using the devices.

As used in connection with the present invention, "thermal processing" (and variations thereof) means controlling (e.g., maintaining, raising, or lowering) the temperature of sample materials to obtain desired reactions. As one form of thermal processing, "thermal cycling" (and variations thereof) means sequentially changing the temperature of sample materials between two or more temperature setpoints to obtain desired reactions. Thermal cycling may involve, e.g., cycling between lower and upper temperatures, cycling between lower, upper, and at least one intermediate temperature, etc.

As used in connection with the present invention, the term "electromagnetic energy" (and variations thereof) means electromagnetic energy (regardless of the wavelength/frequency) capable of being delivered from a source to a desired location or material in the absence of physical contact. Nonlimiting examples of electromagnetic energy include laser energy, radiofrequency (RF), microwave radiation, light energy (including the ultraviolet through infrared spectrum), etc. It may be preferred that electromagnetic energy be limited to energy falling within the spectrum of ultraviolet to infrared radiation (including the visible spectrum).

In one aspect, the present invention provides a method of conducting a thermal cycling process by providing a device including a plurality of process chambers, each process chamber of the plurality of process chambers defining a volume for containing sample material; providing a base plate including a top surface, a bottom surface, and a thermal structure; locating a first major surface of the device in contact with the top surface of the base plate, wherein at least some process chambers of the plurality of process chambers are in thermal communication with the thermal structure when the device is in contact with the top surface of the base plate; providing sample material in the plurality of process chambers; and controlling the temperature of the thermal structure by directing electromagnetic energy at the bottom surface of the base plate while rotating the base plate and the device about the axis of rotation, whereby the temperature of the sample material is controlled.

In another aspect, the present invention provides a method of conducting a thermal cycling process by providing a device including a plurality of process chambers, each process chamber of the plurality of process chambers defining a volume for containing sample material; providing a base plate including a top surface, a bottom surface, and a thermal structure that includes at least one thermoelectric module; locating a first major surface of the device in contact with the top surface of the base plate, wherein the plurality of process chambers are in thermal communication with the thermal structure when the device is in contact with the top surface of the base plate; providing sample material in the plurality of process chambers; and controlling the temperature of the thermal structure by controlling the temperature of the at least one thermoelectric module while rotating the base plate and the device about the axis of rotation, wherein the temperature of the sample material is controlled.

In another aspect, the present invention provides a method of conducting a thermal cycling process by providing a device including a plurality of process chambers, each process chamber of the plurality of process chambers defining a volume for containing sample material; providing sample material in the plurality of process chambers; directing electromagnetic energy into the plurality of process chambers to raise the temperature of the sample material in the plurality of process chambers; and rotating the device about an axis of rotation while directing electromagnetic energy into the plurality of process chambers, wherein the temperature of the sample material in the plurality of process chambers is controlled as the device rotates about the axis of rotation.

In another aspect, the present invention provides a method of processing sample material by providing a device including at least one process chamber array that includes a loading chamber and a first process chamber; providing sample material in the at least one process chamber array, the sample material being provided in the loading chamber of the at least one process chamber array; moving the sample material from the loading chamber to the first process chamber of the at least one process chamber array by rotating the device the device about an axis of rotation; providing a base plate including a top surface, a bottom surface, and a thermal structure; locating a first major surface of the device in contact with the top surface of the base plate, wherein the first process chamber of the at least one process chamber array is in thermal communication with the thermal structure when the device is in contact with the top surface of the base plate; and controlling the temperature of the thermal structure by directing electromagnetic energy at the bottom surface of the base plate while rotating the base plate and the device about the axis of rotation, whereby the temperature of the sample material is controlled.

In another aspect, the present invention comprises a method of conducting a thermal cycling process by providing a device including a plurality of process chamber arrays, each process chamber array of the plurality of process chamber arrays including a loading chamber and a first process chamber; providing a base plate including a top surface, a bottom surface, and a thermal structure that includes at least one thermoelectric module; locating a first major surface of the device in contact with the top surface of the base plate, wherein the first process chamber of at least one process chamber array of the plurality of process chamber arrays is in thermal communication with the thermal structure when the device is in contact with the top surface of the base plate; providing sample material in at least one process chamber array of the plurality of process chamber arrays, the sample material being provided in the loading chamber of the at least one process chamber array; moving the sample material from the loading chamber to the first process chamber of the at least one process chamber array by rotating the device the device about an axis of rotation; and controlling the temperature of the thermal structure by controlling the temperature of the at least one thermoelectric module while rotating the base plate and the device about the axis of rotation, wherein the temperature of the sample material is controlled.

In another aspect, the present invention provides a method of processing sample material by providing a device including a plurality of process chamber arrays, each process chamber array of the plurality of process chamber arrays including a loading chamber and a first process chamber; providing sample material in at least one process chamber array of the plurality of process chamber arrays, the sample material being provided in the loading chamber of the at least one process chamber array; moving the sample material from the loading chamber to the first process chamber of the at least one process chamber array by rotating the device the device about an axis of rotation; directing electromagnetic energy into the first process chamber of the at least one process chamber array to raise the temperature of the sample material in the first process chamber of the at least one process chamber array; and rotating the device about an axis of rotation while directing electromagnetic energy into the first process chamber of the at least one process chamber array, wherein the temperature of the sample material in the first process chamber of the at least one process chamber array is controlled as the device rotates about the axis of rotation.

In another aspect, the present invention provides a device for processing sample material, the device including a substrate that includes first and second major surfaces; a plurality of process chambers in the device, each of the process chambers defining a volume for containing a sample; and a plurality of valves with at least one of the valves located between selected pairs of the process chambers, each valve including an impermeable barrier, wherein the impermeable barrier of each of the valves separates the selected pairs of process chambers.

In another aspect, the present invention provides a device for processing sample material, the device including a substrate that includes first and second major surfaces; a plurality of process chambers in the device, each of the process chambers defining a volume for containing a sample; and a plurality of valves with at least one of the plurality of valves located between selected pairs of the process chambers, each valve including shape memory polymer.

In another aspect, the present invention provides a device for processing sample material, the device including a substrate that includes first and second major surfaces; a plurality of process chambers in the device, each of the process chambers defining a volume for containing a sample; and a seal defining the volume of at least some of the process chambers, wherein the seal comprises shape memory polymer.

In another aspect, the present invention provides a device for processing sample material, the device including a substrate that includes first and second major surfaces; a plurality of process chambers in the device, each of the process chambers defining a volume for containing a sample; and a control pattern on the device, the control pattern including at least one indicator associated with each of the plurality of process chambers, each of the indicators having at least one characteristic indicative of electromagnetic energy to be delivered to each process chamber associated with that indicator, whereby the delivery of the electromagnetic energy to selected process chambers can be controlled.

In another aspect, the present invention provides a method of processing sample material by providing a device including a plurality of process chamber arrays, each of the process chamber arrays including a loading chamber and a process chamber; providing sample material in the loading chamber of at least one of the process chamber arrays; moving the sample material from the loading chamber to the process chamber by rotating the device; providing paramagnetic particles within the sample material located in the process chamber; providing a magnet proximate the device; and rotating the device such that the paramagnetic particles within the sample material are subjected to the magnetic field of the magnet during the rotating.

In another aspect, the present invention provides a sample processing system including a rotating base plate; at least one thermal structure attached to the base plate, the at least one thermal structure including a top surface and a bottom surface; and at least one thermoelectric module in thermal communication with the thermal structure, the at least one thermoelectric module arranged to control the temperature of the thermal structure while the base plate is rotating.

These and other features and advantages of the devices, systems and methods of the invention are described below with respect to illustrative embodiments of the invention.

BRIEF DESCRIPTION OF THE FIGURES

FIGS. 23A & 23B depict an alternative valve structure for use in connection with the devices and methods of the present invention.

FIGS. 24A & 24B depict an alternative valve structure for use in connection with the devices and methods of the present invention.

DETAILED DESCRIPTION OF ILLUSTRATIVE EMBODIMENTS OF THE INVENTION

The present invention provides a device that can be used in methods that involve thermal processing, e.g., sensitive chemical processes such as PCR amplification, ligase chain reaction (LCR), self-sustaining sequence replication, enzyme kinetic studies, homogeneous ligand binding assays, and more complex biochemical or other processes that require precise thermal control and/or rapid thermal variations. The device may include, e.g., a reflective layer, baffle structures, valve structures, capture plugs, thermal indicators, absorptive materials, and other materials or components that facilitate rapid and accurate thermal processing of sample materials in the process chambers of the device.

Although construction of a variety of illustrative embodiments of devices are described below, rotatable sample processing devices according to the principles of the present invention may be manufactured according to the principles described in U.S. Provisional Patent Application Serial No. 60/214,508 filed on Jun. 28, 2000 and titled THERMAL PROCESSING DEVICES AND METHODS; U.S. Provisional Patent Application Serial No. 60/214,642 filed on Jun. 28, 2000 and titled SAMPLE PROCESSING DEVICES, SYSTEMS AND METHODS; U.S. Provisional Patent Application Serial No. 60/237,072 filed on Oct. 2, 2000 and titled SAMPLE PROCESSING DEVICES, SYSTEMS AND METHODS; and U.S. Provisional Patent Application Serial No. 60/284,637 filed on Apr. 18, 2001 and titled ENHANCED SAMPLE PROCESSING DEVICES, SYSTEMS AND METHODS. Other potential device constructions may be found in, e.g., U.S. patent application Ser. No. 09/710,184 filed on Nov. 10, 2000 and titled CENTRIFUGAL FILLING OF SAMPLE PROCESSING DEVICES and U.S. Provisional Patent Application Serial No. 60/260,063 filed on Jan. 6, 2001 and titled SAMPLE PROCESSING DEVICES, SYSTEMS AND METHODS.

Although relative positional terms such as "top" and "bottom" may be used in connection with the present invention, it should be understood that those terms are used in their relative sense only. For example, when used in connection with the devices of the present invention, "top" and "bottom" are used to signify opposing sides of the devices. In actual use, elements described as "top" or "bottom" may be found in any orientation or location and should not be considered as limiting the methods, systems, and devices to any particular orientation or location. For example, the top surface of the device may actually be located below the bottom surface of the device in use (although it would still be found on the opposite side of the device from the bottom surface).

Figure 1:
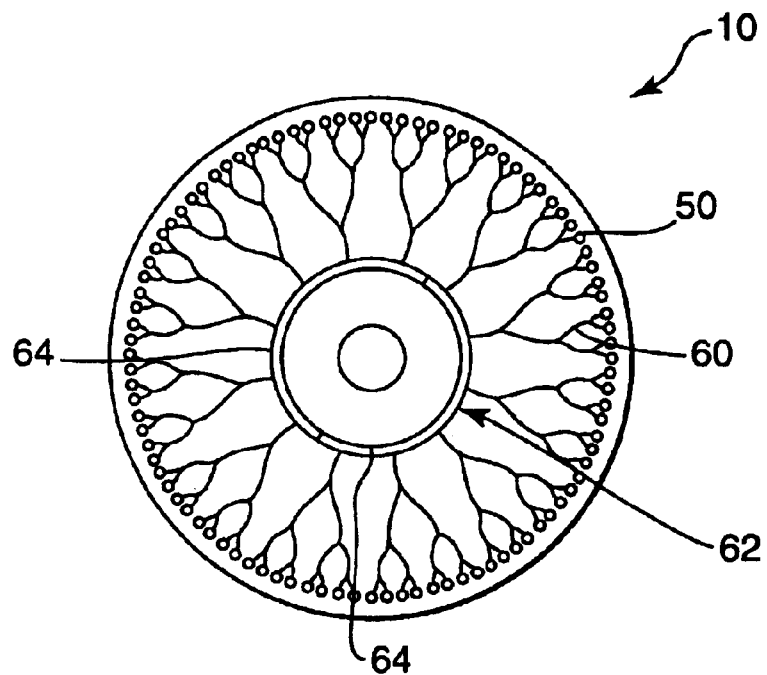
FIG. 1 is a top plan view of one device according to the present invention.
Figure 2:
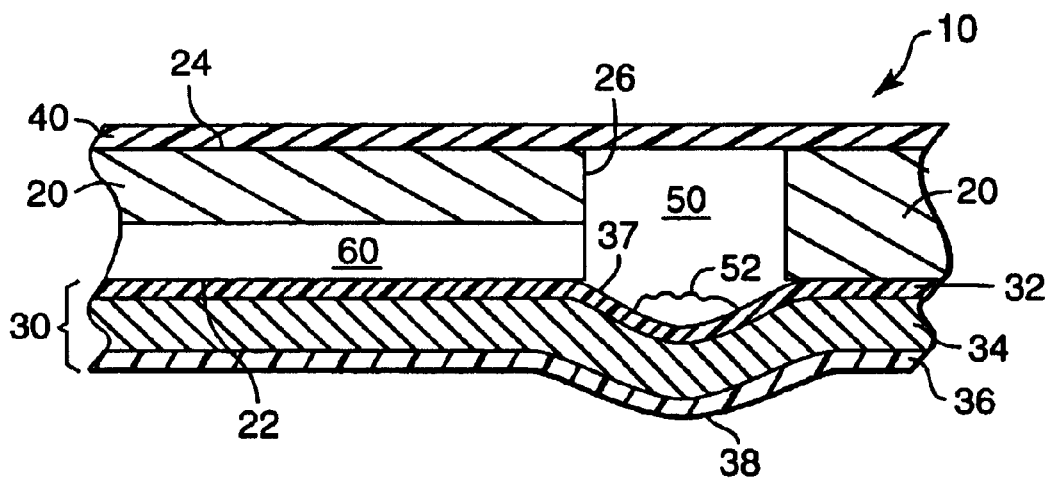
FIG. 2 is an enlarged partial cross-sectional view of a process chamber and distribution channel in the device of FIG. 1.

One illustrative device manufactured according to the principles of the present invention is depicted in FIGS. 1 and 2. The device 10 is preferably in the shape of a circular disc as illustrated in FIG. 1, although any other shape that can be rotated could be used in place of the preferred circular disc. The device 10 of FIGS. 1 and 2 is a multi-layered composite structure including a substrate 20, first layer 30, and a second layer 40.

The device 10 includes a plurality of process chambers 50, each of which defines a volume for containing a sample and any other materials that are to be thermally cycled with the sample. The illustrated device 10 includes ninety-six process chambers 50, although it will be understood that the exact number of process chambers provided in connection with a device manufactured according to the present invention may be greater than or less than ninety-six, as desired.

The process chambers 50 in the illustrative device 10 are in the form of chambers, although the process chambers in devices of the present invention may be provided in the form of capillaries, passageways, channels, grooves, or any other suitably defined volume.

It is preferred that the substrate 20, first layer 30 and second layer 40 of the device 10 be attached or bonded together with sufficient strength to resist the expansive forces that may develop within the process chambers 50 as, e.g., the constituents located therein are rapidly heated during thermal processing. The robustness of the bonds between the components may be particularly important if the device 10 is to be used for thermal cycling processes, e.g., PCR amplification. The repetitive heating and cooling involved in such thermal cycling may pose more severe demands on the bond between the sides of the device 10. Another potential issue addressed by a more robust bond between the components is any difference in the coefficients of thermal expansion of the different materials used to manufacture the components.

Also disclosed in FIG. 2 is a reagent 52 located within the process chamber 50. The reagent 52 may preferably be fixed to a surface of the process chamber 50. The reagent 52 is optional, i.e., some devices 10 may or may not include any reagents 52 loaded in the process chambers 50. In another variation, some of the process chambers 50 may include a reagent 52 while others do not. In yet another variation, different process chambers 50 may contain different reagents.

The illustrated device 10 also includes an optional registration system, whereby the position of the different process chambers 50 can be accurately determined, even as the device 10 is rotated during the processing methods described in more detail below. The registration system may be provided in the form of registration marks 14 on the device 10. Another alternative registration system may involve keying the device 10 such that it can be mounted on, e.g., a rotating spindle, in only one orientation. In such a system, the rotational position of the spindle would then be indicative of the position of the various features on the device 10. Other registration systems will be known to those skilled in the art.

The process chambers 50 are in fluid communication with distribution channels 60 that, together with loading chamber 62, provide a distribution system for distributing samples to the process chambers 50. Introduction of samples into the device 10 through the loading chamber 62 may be accomplished by rotating the device 10 about a central axis of rotation such that the sample materials are moved outwardly due to centrifugal forces generated during rotation. Before the device 10 is rotated, the sample can be introduced into the loading chamber 62 for delivery to the process chambers 50 through distribution channels 60. The process chambers 50 and/or distribution channels 60 may include ports through which air can escape and/or other features to assist in distribution of the sample materials to the process chambers 50. Alternatively, sample materials could be loaded into the process chambers 50 under the assistance of vacuum or pressure.

Alternatively, the distribution system used to deliver sample materials to the process chambers 50 may be "unvented." As used in connection with the present invention, an "unvented distribution system" is a distribution system (i.e., process chamber array) in which the only openings leading into the volume of the distribution channels 60 and the process chambers 50 are located in the loading chamber 62. In other words, to reach the process chamber 50 within an unvented distribution system, sample materials must be delivered to the loading chamber 62. Similarly, any air or other fluid located within the distribution system before loading with sample material must also escape from the distribution system through the loading chamber 62. In contrast, a vented distribution system would include at least one opening outside of the loading chamber. That opening would allow for the escape of any air or other fluid located within the distribution system before loading during distribution of the sample material to the process chambers 50.

Moving sample material through within sample processing devices 10 that include unvented distribution systems may be facilitated by alternately accelerating and decelerating the device 10 during rotation, essentially burping the sample materials through the channels 60 and into process chambers 50. The rotating may be performed using at least two acceleration/deceleration cycles, i.e., an initial acceleration, followed by deceleration, second round of acceleration, and second round of deceleration.

It may further be helpful if the acceleration and/or deceleration are rapid. The rotation may also preferably only be in one direction, i.e., it may not be necessary to reverse the direction of rotation during the loading process. Such a loading process allows sample materials to displace the air in those portions of the system that are located farther from the center of rotation of the device 10 than the opening into the system. One advantage of an unvented distribution system, i.e., a distribution system including at least some channels and process chambers outside (radially) of any vents, is that leakage from those vents is prevented.

The actual acceleration and deceleration rates may vary based on a variety of factors such as temperature, size of the device, distance of the sample material from the axis of rotation, materials used to manufacture the devices, properties of the sample materials (e.g., viscosity), etc. One example of a useful acceleration/deceleration process may include an initial acceleration to about 4000 revolutions per minute (rpm), followed by deceleration to about 1000 rpm over a period of about 1 second, with oscillations in rotational speed of the device between 1000 rpm and 4000 rpm at 1 second intervals until the sample materials have traveled the desired distance.

The distribution channel 60 illustrated in FIG. 2 is formed in the substrate 20 of the illustrative device 10. The channel 60 is in fluid communication with the process chamber 50 and is also in fluid communication with the loading chamber 62. The channel 60 may be formed by a variety of techniques, preferably a microreplication technique. Examples of suitable microreplication techniques include micromilling, injection molding, vacuum molding, laser ablation, photolithography, thermoforming, embossing, etc.

The illustrated device 10 includes a loading chamber 62 with two sub chambers 64 that are isolated from each other. As a result, a different sample can be introduced into each subchamber 64 for loading into the process chambers 50 that are in fluid communication with the respective subchamber 64 of the loading chamber 62 through distribution channels 60. It will be understood that the loading chamber 62 may contain only one chamber or that any desired number of subchambers 64, i.e., two or more subchambers 64, could be provided in connection with the device 10.

FIG. 2 is an enlarged cross-sectional view of a portion of the device 10 including one of the process chambers 50 and a distribution channel 60. The substrate 20 includes a first major side 22 and a second major side 24. Each of the process chambers 50 is formed, at least in part in this embodiment, by a void 26 formed through the substrate 20. The illustrated void 26 is formed through the first and second major sides 22 and 24 of the substrate 20.

The substrate 20 is preferably polymeric, but may be made of other materials such as glass, silicon, quartz, ceramics, etc. Furthermore, although the substrate 20 is depicted as a homogenous, one-piece integral body, it may alternatively be provided as a non-homogenous body of, e.g., layers of the same or different materials. For those devices 10 in which the substrate 20 will be in direct contact with the sample materials, it may be preferred that the material or materials used for the substrate 20 be non-reactive with the sample materials. Examples of some suitable polymeric materials that could be used for the substrate in many different bioanalytical applications may include, but are not limited to, polycarbonate, polypropylene (e.g., isotactic polypropylene), polyethylene, polyester, etc.

A first layer 30 is provided on one side of the substrate 20 in the illustrated embodiment and preferably includes a metallic sub-layer 34 located between an optional passivation layer 32 and an optional outer protective layer 36. The first layer 30 thus defines a portion of the volume of the process chamber 50. A second layer 40 is provided on the opposite side of the substrate 20 to define the remainder of the volume of the process chamber 50.

It may be preferred that at least a portion of the materials defining the volume of the process chamber 50 be transmissive to electromagnetic energy of selected wavelengths. The selected wavelengths may be determined by a variety of factors, for example, electromagnetic energy designed to heat and/or interrogate a sample in the process chamber 50, electromagnetic energy emitted by the sample (e.g., fluorescence), etc.

In the device 10, where the first layer 30 includes a metallic sub-layer 34, it may be preferred that the materials used for the second layer 40 of the device 10 transmit electromagnetic energy of selected wavelengths. By providing a transmissive process chamber 50, a sample in the chamber can be interrogated by electromagnetic energy of selected wavelengths (if desired) and/or electromagnetic energy of the selected wavelengths emanating from the sample can be transmitted out of the process chamber 50 where it can be detected by suitable techniques and equipment. For example, electromagnetic energy may be emitted spontaneously or in response to external excitation. A transmissive process chamber 50 may also be monitored using other detection techniques, such as color changes or other indicators of activity or changes within the process chambers 50.

In some instances, however, it may be desirable to prevent the transmission of selected wavelengths of electromagnetic energy into the process chambers. For example, it may be preferred to prevent the transmission of electromagnetic energy in the ultraviolet spectrum into the process chamber where that energy may adversely impact any reagents, sample materials, etc. located within the process chamber.

In the device illustrated in FIG. 2, the first layer 30 preferably includes a structure such that the first layer 30 deviates from an otherwise flat surface on at least the surface 37 facing the interior volume of the process chamber 50. For example, the first layer 30 may be cast, molded, thermoformed, embossed or otherwise manufactured to produce an interior surface 37 that has a desired shape. The shape of the structure formed in the first layer 30 may vary, although it may be preferred that the shape of the interior surface 37 facing the volume of the process chamber 50 be concave (e.g., parabolic) such that some focusing of any electromagnetic energy reflected from that surface may be effected.

It may also be preferred that the exterior surface of the first layer 30, i.e., the surface that faces away from the substrate 20, also include baffle structure 38 such that airflow is disrupted over the first layer 30 as the device 10 is rotated. By disrupting airflow over the first layer 30, heat transfer of energy out of the first layer 30 into the surrounding atmosphere may be enhanced. The illustrated first layer 30 includes a baffle structure 38 with a shape that corresponds to the shape of the interior surface 37 of the metallic sub-layer 34, although the shape of the baffle structure 38 may, alternatively, be different than the shape of the interior surface 37.

The metallic sub-layer 34 is preferably not exposed to the interior volume of the process chamber 50 to prevent contamination of any sample by the metal or metals used in the metallic sub-layer 34. The optional passivation layer 32 is provided to prevent exposure of the metallic sub-layer 34 to the interior volume of the process chamber 50. The materials used in the passivation layer 32 are preferably capable of secure attachment to both the metallic sub-layer 34 and the materials used in for the substrate 20 by, e.g., adhesives, heat sealing, etc. It is also preferred that the materials used for the passivation layer 32 be non-reactive with any materials in the samples located within the process chambers 50. Examples of suitable materials for the passivation layer 32 may include, but are not limited to, thermoplastics, polypropylene (e.g., isotactic polypropylene), polyethylene, polyester, etc.

Although the passivation layer 32 is depicted as a single homogenous structure, it may be formed as two or more layers of the same or different materials. For example, an adhesion promoting layer may be used to enhance adhesion of the passivation layer 32 to, e.g., the metallic sub-layer 34. The adhesion promoting layer may be, e.g., heat-sealable, a pressure sensitive adhesive, hot melt adhesive, curable adhesive, etc.

Further, although the passivation layer 32 is preferably substantially coextensive with the metallic sub-layer 34, the passivation layer 32 may be provided in a discontinuous pattern on the metallic sub-layer 34, with the discontinuous pattern preventing exposure of the metallic sub-layer 34 to the interiors of the process chambers 50.

The materials and/or thickness of the passivation layer 32 may also preferably be selected to transmit electromagnetic energy of selected wavelengths to allow for reflection from the underlying metallic sub-layer 34 without significant absorption or diffusion. This may be particularly true where the shape of the interior surface of the metallic sub-layer 34 is designed to provide some focusing of electromagnetic energy. It may also be preferred that the passivation layer 32 be relatively thin so that the transfer of thermal energy from any sample materials in the process chambers 50 into the metallic sub-layer 34 is not substantially inhibited (so that energy can be dissipated into the atmosphere or another structure). For example, where the passivation layer 32 is an isotactic polypropylene, the layer 32 may preferably be about 0.005 inches (0.13 mm) or less, more preferably about 0.002 inches (0.05 mm) or less.

The metallic sub-layer 34 may take a variety of forms. Although the layer 34 is depicted as a single, homogenous structure, it may be provided as a multi-layer structure of two or more layers. It may be preferred that the metallic sub-layer 34 consist essentially of one or more metals. Examples of suitable metals that could be used in the metallic sub-layer 34 include aluminum, stainless steel, copper, titanium, silver, gold, tin, etc. One potential advantage of a metallic sub-layer 34 is that the metallic layer may assist in equilibrating the temperature between process chambers 50 by conducting heat away from hot spots or into cool spots on the device 10.

The thickness of the layer 34 may be selected to provide a relatively low thermal mass to facilitate rapid thermal cycling of the samples in the process chambers 50. The desire for low thermal mass of the metallic sub-layer 34 may, however, be balanced by a number of factors.

For example, the desire for a metallic sub-layer 34 with low thermal mass may be balanced by a desire for thermal conductivity across the device 10, e.g., between chambers 50. That thermal conductivity across the device 10 can contribute to chamber-to-chamber temperature uniformity, as well as comparable chamber-to-chamber temperature transition rate.

Another factor to balance with the desire for reduced thermal mass is the need for integrity of the first layer 30. In many devices 10, the metallic sub-layer 34 may provide a significant portion, or even a majority, of the structural integrity of the first layer 30. A metallic sub-layer 34 that is too thin or manufactured of the wrong metal or metals may not provide sufficient integrity for the device 10. For example, if the metallic sub-layer 34 is to be formed (e.g., stamped, etc.) to assist in the formation of the process chambers 50, distribution channels (see, e.g., FIG. 3), baffle structure 38, etc., the metal or metals and their thickness should be amenable to such processes.

The barrier properties of the metal or metals and their thickness used in the metallic sub-layer 34 may also need to be balanced against the desire for reduced thermal mass. For example, the metallic sub-layer 34 may need to be thick enough to provide sufficient vapor barrier properties in response to the thermal processing taking place in the process chambers 50 or to increase the shelf-life of the device 10 where, e.g., moisture sensitive reagents 52 are pre-loaded within the process chambers 50.

Yet another factor to consider when selecting the thickness of the metallic sub-layer 34 and the metal or metals in it may be the need for reflectivity. If the metallic sub-layer is too thin and/or formed of the wrong metals, it may not exhibit sufficient reflectivity over the selected wavelengths of electromagnetic energy.

When balancing all of the concerns discussed above, it may be preferred that the thickness of the metallic sub-layer 34 be about 0.04 inches (1 mm) or less, more preferably about 0.02 inches (0.5 mm) or less, and still more preferably about 0.010 inches (0.25 mm) or less. At the lower end of the range, the thickness of the metallic sub-layer 34 may preferably be sufficient to provide the desired reflectivity and/or structural integrity to the first layer 30 of the device 10. For example, it may be preferred that the metallic sub-layer 34 be at least about 0.0005 inches (0.013 mm) thick, more preferably at least about 0.001 inches (0.025 mm) thick, and still more preferably about 0.003 inches (0.075 mm).

The actual range of suitable thickness for the metallic sub-layer 34 may depend, at least in part, on the thermal properties of the metal or metals used to form the layer. Where the layer 34 is formed of aluminum, the layer 34 may preferably have a thickness in the range of, e.g., about 0.025 millimeters (mm) to about 0.25 mm.

As an alternative, the reflective properties desired in the devices of the present invention may be provided by non-metallic reflective materials. For example, multi-layer polymeric films may be used to provide the desired reflectivity or to enhance the reflectivity of metallic layers used in the devices of the present invention. Reflective polymeric films that may be useful in connection with the present invention are described in U.S. Pat. No. 5,882,774 (Jonza et al.); U.S. Pat. No. 6,101,032 (Wortman et al.); and International Publication Nos. WO 99/36809, WO 99/36810, WO 99/36812, WO 99/36248, and WO 99/36258.

Also depicted in FIG. 2 is an optional protective layer 36 provided on the surface of the metallic sub-layer 34 that faces away from the process chamber 50. The protective layer 36 may protect the integrity of the metallic sub-layer 34 and/or may increase the toughness of the device 10. Another potential advantage of the protective layer 36 is the reduction or prevention of oxidation of the metallic sub-layer 34 (which could adversely affect the rate of thermal energy transfer out of the metallic sub-layer 34).

Still another advantage of providing both an outer protective layer on one side of a metallic sub-layer and a passivation layer on the other side of the metallic layer is that the formability of the first layer 30 may be improved. If, for example, a side of the device including a metallic sub-layer 34 is to be formed to provide process chambers (see, e.g., FIG. 3), distribution channels, baffle structures, or any other features, the formability of the side including the metallic sub-layer may be improved if the metallic sub-layer is covered on both sides. This may be especially true with forming processes that involve molding (e.g., plug molding, vacuum molding, thermoforming, etc.).

The thickness and the materials used for the protective layer 36 are preferably such that the layer 36 does not substantially affect the transfer of thermal energy out of the metallic sub-layer 34. An example of one suitable protective layer 36 is a thin coating of epoxy with a thickness of about 0.001 inches (0.025 mm). Other examples of non-metallic protective layer materials include, but are not limited to, polyester, polycarbonate, polypropylene, polyethylene, etc.

One product that may meet many of the above criteria for the first layer 30 is a heat sealing metal foil available from Marsh Biomedical Products, Inc., Rochester N.Y. under the designation AB-0559.

Figure 3:
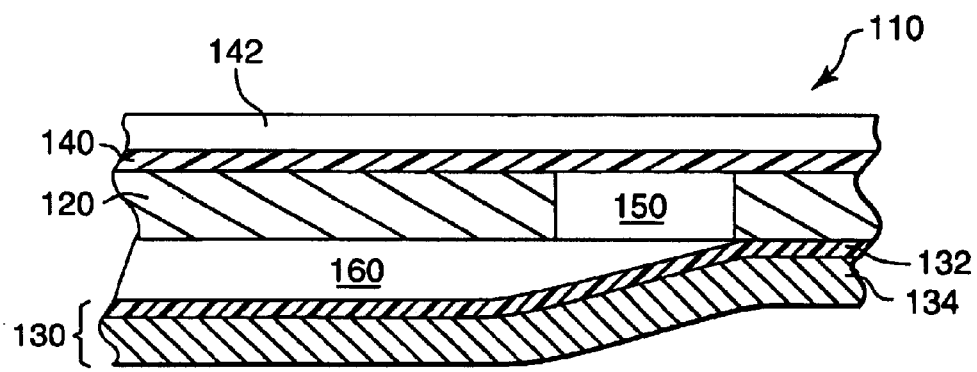
FIG. 3 is an enlarged partial cross-sectional view of an alternate device according to the present invention, illustrating a process chamber, distribution channel and a baffle structure.
Figure 4:
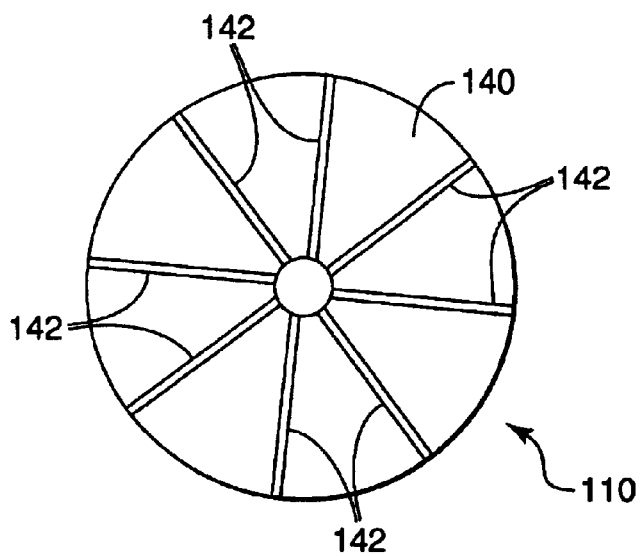
FIG. 4 is a plan view of one major side of the device of FIG. 3.

FIG. 3 is an enlarged partial cross-sectional view of another illustrative embodiment of a device 110 according to the present invention, the second layer 140 of which is illustrated in the plan view provided in FIG. 4. The device 110 includes a substrate 120, first layer 130 and second layer 140 constructed in much the same manner as the device 10 described above. It should be noted that the first layer 130 of the device 110 does not include the optional outer protective layer of device 10, but is preferably constructed of a passivation layer 132 and a metallic sub-layer 134.

Among the other differences between the device 10 and device 110 are that the distribution channel 160 that is in fluid communication with the process chamber 150 is formed primarily as a structure in the first layer 130. The structure required to form the channel 160 in the first layer 130 can also provide a baffle structure 138 on the bottom of the device 110. The baffles 138 formed in the bottom layer 130 could take on the form of the distribution channels 160 required to distribute sample materials to the process chambers 150. One example of such a pattern is illustrated by the channels 60 in FIG. 1.

Another difference is that the second layer 140 may also include baffle structures 142 designed to increase the turbulence in airflow over the device 110 as it is rotated. The baffles 142 are seen in FIGS. 3 and 4. Although the illustrated baffles 142 on the cover layer 140 are arranged radially on the device 110, it will be recognized that they could be provided in any pattern designed to increase turbulent flow or other flow that improves heat transfer out of the device 110. The baffles 142 may be integral with the second layer 140 or they may be provided as separate articles adhered or otherwise attached to the second layer 140.

Figure 4A:
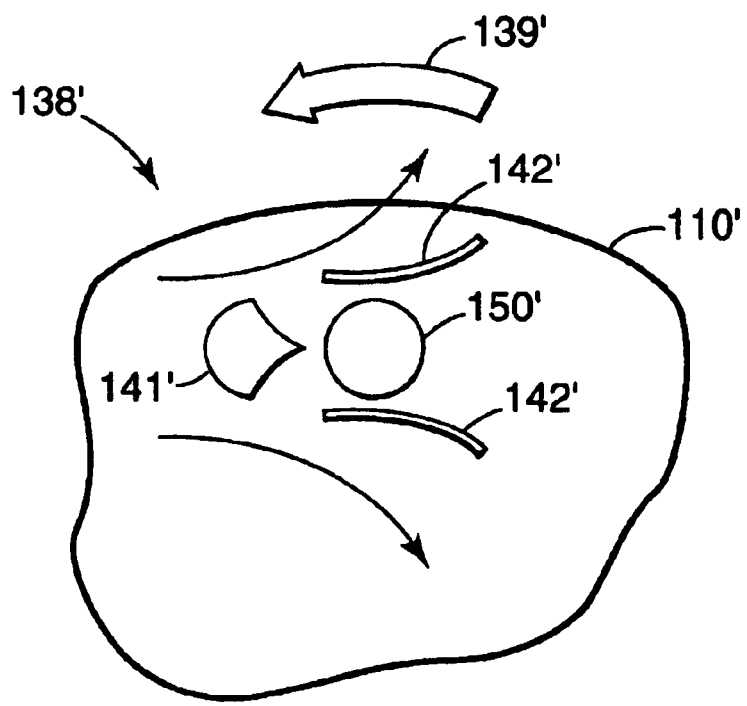
FIG. 4A is a schematic diagram of one baffle structure and airflow through the structure as a sample processing device is rotated in one direction.
Figure 4B:
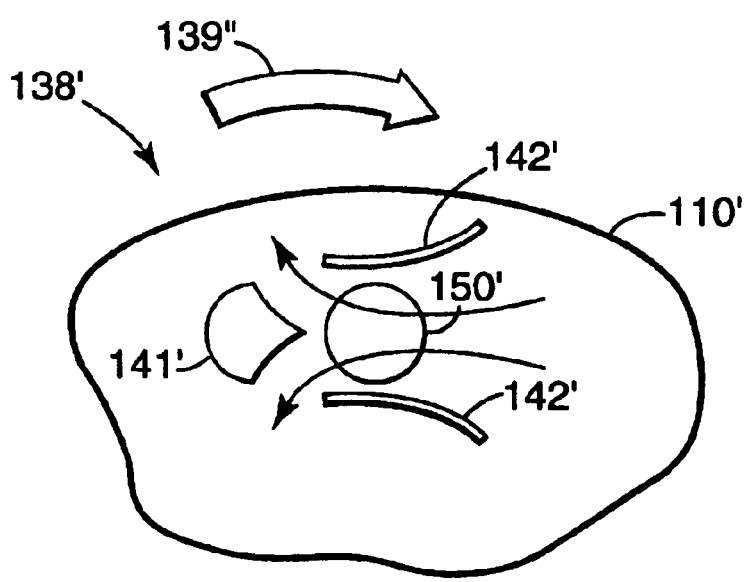
FIG. 4B is a schematic diagram of the baffle structure of FIG. 4A depicting airflow when the sample processing device is rotated in the opposite direction.

One variation on the baffle structures discussed thus far in connection with devices of the present invention is depicted in FIGS. 4A & 4B. Rather than induce turbulent airflow over substantially the entire surface of the devices, it may be desirable to provide controlled airflow over selected portions of the device 110'. That selected portion may preferably include, e.g., a process chamber 150' as illustrated in FIGS. 4A & 4B. In some embodiments, it may be preferred to provide some or all of the process chambers 150' with an individual baffle structure 138'.

In contrast to providing structures that increase turbulent flow over substantially the entire surface of the device, the baffle structure 138' depicted in FIGS. 4A & 4B may offer more control over airflow in selected areas. Where a large number of baffle structures 138' are provided, the end result may, however, still be turbulent flow over substantially the entire surface of the device.

The baffle structure 138' is directional, i.e., when the device 110' is moved in the direction of arrow 139', airflow is diverted over and/or around the process chamber 150' by a fairing 141' and diverters 142'. As a result, the baffle structure 138' may create a pool of relatively stagnant air over the process chamber 150', thereby potentially improving the speed with which the process chamber 150' may heated to a desired temperature.

When the device 110' is rotated in the opposite direction as indicated by arrow 139" in FIG. 4B, airflow over the process chamber 150' may be enhanced as the diverters 142' operate to capture or scoop air and direct it over the process chamber 150'. The baffle structure 138' may enhance convective air cooling of the process chamber 150' when rotated in direction 139", which is opposite the direction 139' of FIG. 4A. That enhanced convective cooling provides for increased thermal energy transfer out of the process chamber 150' as compared to devices rotated without the directional baffle structure.

The fairing 141' may preferably include a narrow leading edge when rotated in direction 139" to enhance airflow over the process chamber 150'. Many alternative structures may be used in place of those depicted in FIGS. 4A & 4B. For example, the relatively aerodynamic shape of the fairing 141' may be replaced by, e.g., one or more posts or other structures that may be less aerodynamic, but effective to create the desired pool of stagnant air over process chamber 150'. Likewise, the diverters 142' may be provided in any suitable form that provides the desired protection from airflow in one direction and concentration of airflow in the opposite direction.

Figure 5:
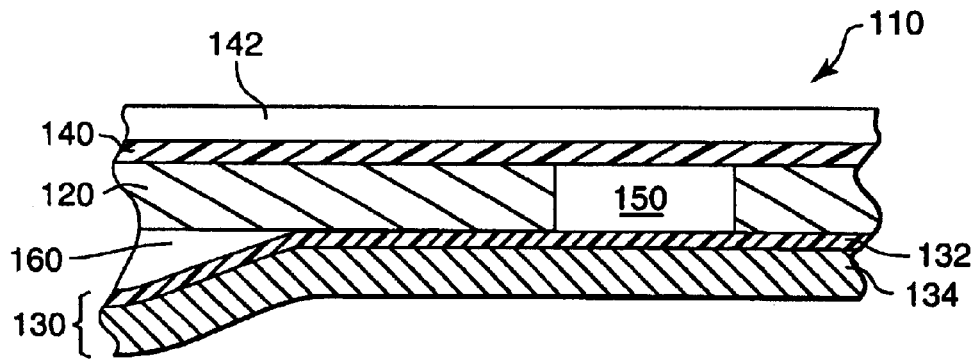
FIG. 5 is an enlarged partial cross-sectional view of a process chamber and distribution channel in the device of FIG. 3 after isolation of the process chamber.

FIG. 5 is another enlarged partial cross-sectional view of the device 110 of FIGS. 3 and 4. This figure illustrates one technique for sealing or isolating the process chamber 150 to, e.g., prevent cross-contamination or diffusion between process chambers 150 in the device 110 after the process chambers 150 have been loaded with sample material. The illustrated technique involves closing the channel 160 by compressing the first layer 130 against the substrate 120. The sealing of the channel 160 may be accomplished mechanically, i.e., by simply crushing the channel 160, or it may be accompanied by the application of heat to enhance adhesion of the first layer 130 to the substrate 120. Alternatively, sufficient isolation may be achieved by continuously rotating the device during processing, such that the sample materials are retained in the process chambers by centrifugal forces.

The sealing of distribution channels may be performed for a variety of purposes in addition to isolating process chambers after distribution of sample materials. For example, selected distribution channels may be sealed before distribution of sample material to reduce the volume of sample material needed to fill the process chambers that remain in fluid communication with the distribution system. In another approach, the tests to be performed using the devices may be customized by sealing selected distribution channels before distributing the sample materials into the process chambers.

Figure 6:
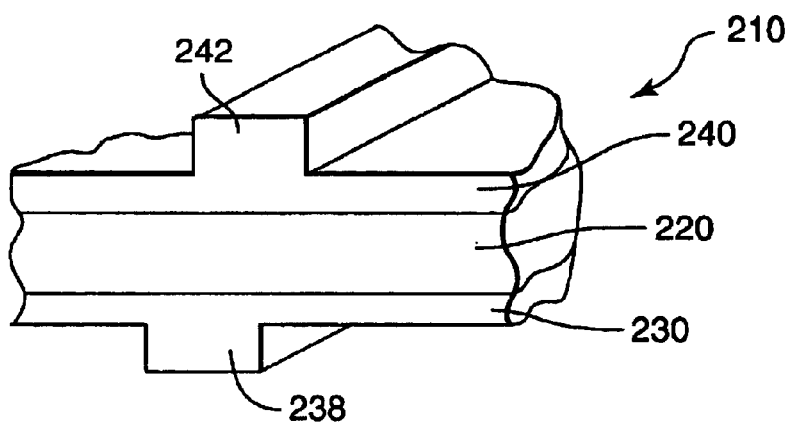
FIG. 6 is a perspective view of a portion of one edge of another alternative device according to the present invention.
Figure 7:
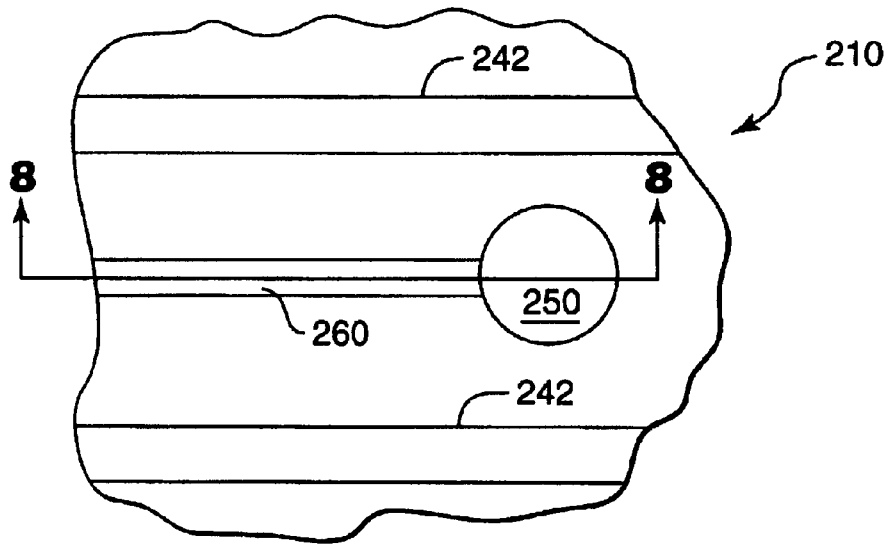
FIG. 7 is a plan view of a portion of the device of FIG. 6 including a process chamber, a distribution channel and baffles.
Figure 8:
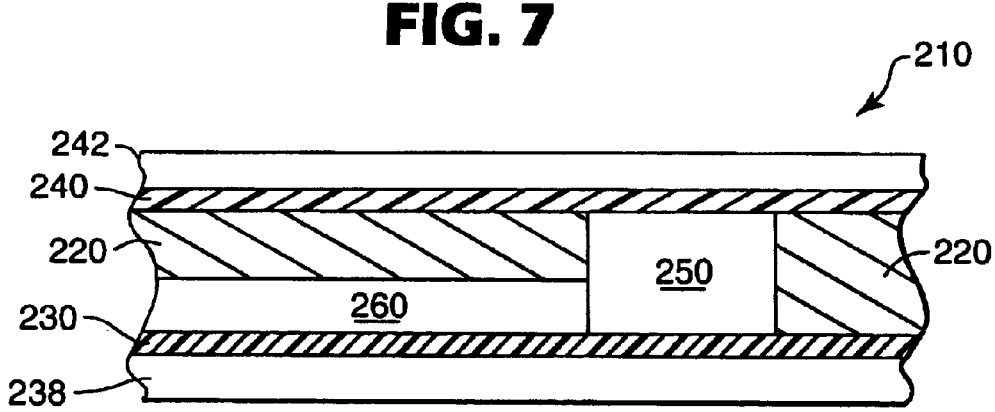
FIG. 8 is a cross-sectional view taken along line 8—8 in FIG. 7.

FIGS. 6–8 depict yet another illustrative embodiment of a device 210 manufactured according to the present invention. The device 210 includes a substrate 220, first layer 230 and second layer 240. FIG. 6, a perspective view of a portion of one edge of the device 210, illustrates a baffle 238 provided in the first layer 230 and a baffle 242 in the second layer 240. As a result, both major sides of the device 210 include at least one baffle, preferably two or more baffles, to increase turbulent flow over those surfaces.

Referring to FIG. 7, a plan view of a portion of the device 210 including a process chamber 250 and a distribution channel 260 in fluid communication with the process chamber 250. FIG. 8 is a cross-sectional view taken along line 8—8 in FIG. 7, and illustrates the process chamber 250 and distribution channel 260, both of which are formed in the substrate 220 by any suitable technique, preferably a microreplication technique. Examples of suitable microreplication techniques include micromilling, injection molding, vacuum molding, laser ablation, photolithography, thermoforming, embossing, etc. The process chamber 250 is formed primarily by a void formed through the substrate 220. Alternatively, the process chamber 250 may be formed by a depression formed through only a portion of the thickness of the substrate 220.

The first layer 230 of the device 210 may or may not include any metals or metallic sub-layers as discussed in connection with the devices 10 and 110 above. Also illustrated in FIG. 8 are a baffle 238 on the first layer 230 and a baffle 242 on the second layer 240.

Figure 9:
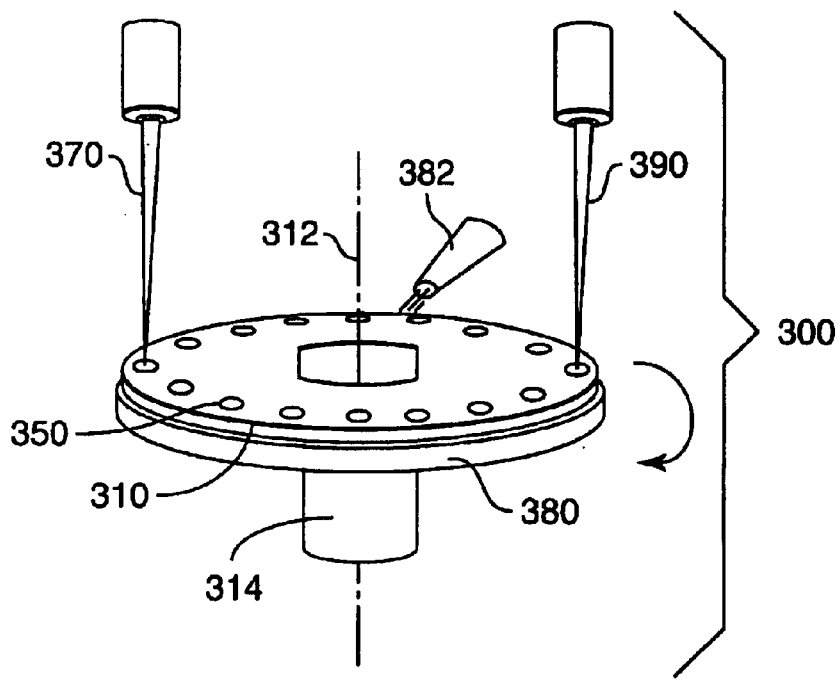
FIG. 9 is a schematic diagram of one thermal processing system according to the present invention.

One illustrative system for accomplishing a thermal cycling process using a device according to the present invention is schematically depicted in FIG. 9. The system 300 includes a device 310 located on a spindle 314 that rotates the device about an axis 312. The device includes process chambers 350 into which a sample material is distributed by, e.g., distribution channels as discussed above or any other suitable techniques and/or structures.

After distribution of the sample material into the process chambers, individual chambers 350 can be selectively heated by suitable electromagnetic energy supplied by an electromagnetic energy source 370 that heats the materials in the process chambers 350. The electromagnetic energy source 370 is preferably remote from the device 310, i.e., it is not located on the device 310. Examples of some suitable electromagnetic energy sources may include, but are not limited to, lasers, broadband electromagnetic energy sources (e.g., white light), etc. The electromagnetic energy source 370 may provide electromagnetic energy continuously or intermittently based on a variety of factors, e.g., the desired temperature of the sample materials, the rate at which thermal energy is removed from each process chamber, the desired rate of temperature change, whether the process chambers include a reflective component, etc. If the electromagnetic energy source 370 is cycled or otherwise varied, the registration system discussed above may be used to deliver a selected amount of electromagnetic energy to selected process chambers.

As the device 310 rotates, it is preferred that the airflow over the surface of the device 310 assists in cooling the sample materials in the process chambers 350 to a selected base temperature from the upper target temperature to which the sample materials are heated by the electromagnetic energy from the source 370. In some systems, one or both surfaces of the device 310 may be exposed to the atmosphere to also assist in cooling. The system 300, however, includes an optional base plate 380 that may be held at a lower temperature. By holding the bottom of the device 310 in contact with the base plate 380, it may be possible to assist in cooling the sample materials in the process chambers 350 between heating cycles as the device 310 rotates during processing. If a base plate 380 is used to assist in thermal control, it may be helpful to use a device 310 incorporating a metallic layer proximate the base plate 380 to improve thermal conductivity between the base plate and the device 310.

In other systems, it may be desirable to promote both heating and cooling of the process chambers through the base plate 380. For example, heating and cooling may be facilitated by incorporating thermoelectric modules (e.g., Peltier elements, resistive heaters, etc.) in the base plate 380 underneath each of the process chambers 350. A thermoelectric module may be provided in the form of a ring located beneath the process chambers 350 or a number of individual thermoelectric modules may be used in connection with base plate 380. The heating of process chambers 350 using base plate 380 may be performed in connection with heating using electromagnetic energy source 370 to provide even faster heating and/or more uniform temperature distribution of the process chambers 350. Thus, the control over sample material temperature may be accomplished by simultaneously delivering electromagnetic energy to the process chambers 350 and controlling the temperature of thermoelectric modules above which the process chambers 350 are located.

The system 300 depicted in FIG. 9 also includes an optional additional temperature control mechanism in the form of a fluid source 382, e.g., pressurized air or any other suitable fluid, that can be directed at the surface of the device 310. The fluid used can be either heated or cooled to a desired temperature. Where it is desired to cycle the sample materials between upper and lower temperatures, the fluid may be provided at the lower temperature. Although depicted as being directed at only one surface of the device 310, it will be understood that the fluid may be directed at both surfaces of the device if desired.

The system 300 may also include various other components such as a detection system 390 provided to detect the results of processing of the sample materials in the process chambers 350. For example, the detection system and method may involve active interrogation of the process chambers 350 to detect fluorescent reaction products in the chambers as the device 310 rotates. The detection may be qualitative or quantitative. Other detection systems may be provided to monitor, e.g., the temperatures or other properties of the materials in the process chambers 350.

As the thermal cycling method is performed, the temperature within the process chambers 350 may be monitored to control the application of energy into the chambers 350. Among the variables that may be manipulated to control the sample material temperatures in the device 310 include the intensity of the laser or other light source, the rotational speed of the device 310 (which can affect the cooling rate and the dwell time of each of the process chambers in the laser or other light source), the temperature of the base plate 380 (or any components such as thermoelectric modules located in the base plate 380), and the temperature and pressure of the fluid source 382.

If the device 310 includes an unvented distribution system, another advantage of rotating the device 310 during heating is that, as the temperature of the sample materials rises and vapor is formed, it must travel upstream, i.e., towards the axis of rotation of the device 310 (where the only opening into the distribution system is located). Once outside of the chamber 350, however, the thermal energy dissipates, causing the vapors to condense. The condensed sample materials are then returned to the sample chambers 350 due to the centrifugal forces provided by the rotation. The end result is that the sample materials are, for the most part, retained in the process chambers 350, even during rapid heating that may cause some vaporization.

Figure 9A:
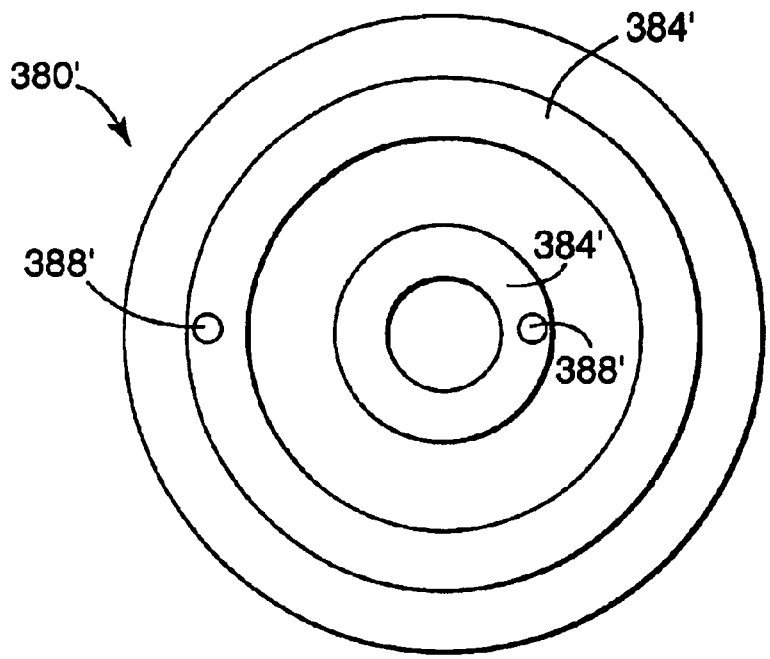
FIG. 9A is a plan view of an alternative base plate for a thermal processing system according to the present invention.
Figure 9B:
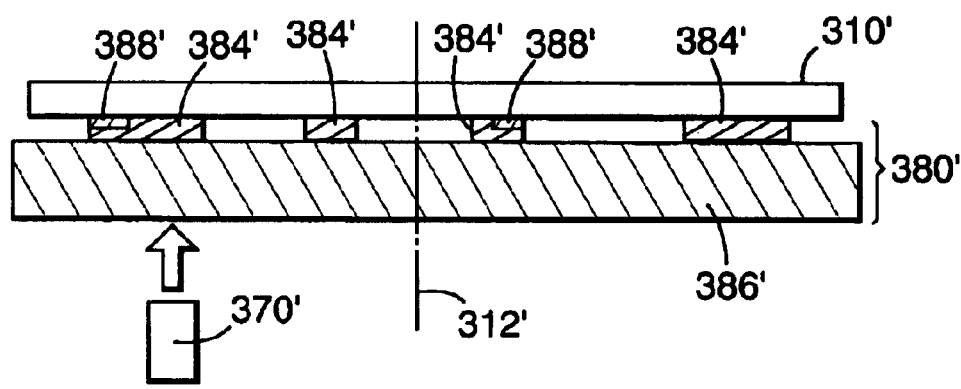
FIG. 9B is a cross-sectional view of the base plate of FIG. 9A with a sample processing device 310' located thereon.

FIGS. 9A and 9B depict an alternative base plate 380' that includes at least one thermal structure 384' that may preferably be constructed of a material that absorbs electromagnetic energy. The thermal structures 384' are in thermal communication with at least some of the process chambers of device 310' (see FIG. 9B) such that heating or cooling of the thermal structures 384' can cause corresponding temperature variations in those process chambers. In the depicted embodiment, the thermal structures 384' are located in contact with the bottom surface of the device 310' and at least some of the process chambers contained therein.

The thermal structures 384' may preferably be heated by an electromagnetic energy source 370' that, in the depicted embodiment, is located on the opposite side of the thermal structures 384' from the device 310'. The electromagnetic energy source 370' directs electromagnetic energy at the bottom surface of the thermal structures 384'. The thermal structures 384' absorb at least some of the electromagnetic energy from source 370' and convert that electromagnetic energy into thermal energy (such that the temperature of the thermal structure 384' increases). The thermal energy in thermal structure 384' is transferred between the device 310' and the thermal structures 384' primarily by conduction.

Although base plate 380' is depicted with two thermal structures 384', it will be understood that the base plate 380' could include any number of thermal structures 384' necessary to transfer thermal energy to or from the selected process chambers in a device 310'. Further, it may be preferred that, where more than one thermal structure 384' is provided, the thermal structures 384' be independent of each other such that no significant amount of thermal energy is transferred between the different independent thermal structures 384'.

The electromagnetic energy source 370' may be in a form that provides electromagnetic energy to only one thermal structure 384' at a time, or it may be capable of heating two or more thermal structures 384' simultaneously. If heating of different thermal structures 384' at different times is desired, it may be desirable to provide a separate electromagnetic energy source 370' dedicated to each thermal structure 384', to move a single energy source 370' such that it is positioned facing the thermal structure 384' to be heated, to provide a shuttering system that provides electromagnetic energy to the necessary thermal structure 384' at the selected time, etc.

The thermal structures 384' may be constructed of a variety of materials, provided the materials possess sufficient thermal conductivity and absorb electromagnetic energy generated by the electromagnetic source 370' at sufficient rates. In addition, it may also be desirable that the material or materials used for the thermal structures 384' have sufficient heat capacity to provide a heat capacitance effect. Examples include, but are not limited to: aluminum, copper, gold, etc. If the thermal structures 384' are constructed of materials that do not, themselves, absorb electromagnetic energy at a sufficient rate, it may be preferred that the thermal structures 384' include a material that improves energy absorption. Fore example, the thermal structures 384' may be coated with an electromagnetic energy absorptive material such as carbon black, polypyrrole, inks, etc.

One potential advantage of using thermal structures 384' in conjunction with the electromagnetic source 370' is that compatibility between the electromagnetic energy source and any reagents or other materials located within the process chambers of the device 310' may be improved. The thermal structures 384' may preferably be opaque to the electromagnetic energy produced by source 370'. As a result, materials within the process chambers may be substantially shielded from direct exposure to the electromagnetic energy that could, in some instances, be detrimental to the desired reactions.

Although the thermal structures 384' are depicted as being located on the top surface of a sub-plate 386', it will be understood that any suitable design that incorporates thermal structures 384' could be used. For example, the thermal structures 384' could be embedded in the sub-plate 386' or no sub-plate 386' could be provided (with the thermal structures 384' interconnected by, e.g., a series of radial struts or other structures). Where a sub-plate 386' is used, however, it may preferably be transmissive to the electromagnetic energy, such that the electromagnetic energy is able to reach the thermal structures 384' to provide the desired thermal heating effect.

Alternatively, the sub-plate 386' may include openings that expose selected portions of the thermal structures 384' to the electromagnetic energy provided by electromagnetic energy source 370'. Where the sub-plate 386' includes openings to expose the bottom surface of the thermal structures 384', the materials of the sub-plate 386' may be opaque to the electromagnetic radiation from the electromagnetic source 370'.

It may further be desirable that the thermal structures 384' be relatively thermally isolated from the sub-plate 386' such that only limited amounts (if any) of the thermal energy in the thermal structures 384' is transferred to the sub-plate 386'. That thermal isolation may be achieved, for example, by manufacturing the sub-plate 386' of materials that absorb only limited amounts of thermal energy, e.g. polymers, etc.

The base plate 380' may also optionally include sensors to detect the temperature of the thermal structures 384'. FIGS. 9A and 9B depict two sensors 388' located in contact with the thermal structures 384' and information from the sensors 388' may be used to control the amount of energy provided by the electromagnetic energy source 370' or to control the rate and/or duration of rotation of the base plate 380' as a part of any system control over both heating and cooling of the thermal structures 384'. Alternatively, the thermal structure temperature or the temperature within the process chambers on device 310' may be monitored remotely by, e.g., infrared emissions, etc.

Although the base plate 380' of FIGS. 9A and 9B includes thermal structures 384' in the form of substantially continuous circular rings, the thermal structures 384' may alternatively be provided as a series of discontinuous thermal elements, e.g., circles, squares, located beneath process chambers on the device 310' that are to be heated by conduction. One advantage, however, of a continuous ring thermal structure is that temperature of each thermal structure 384' may equilibrate during heating, thereby potentially improving chamber-to-chamber temperature uniformity for all process chambers located above the continuous thermal structure.

Methods of using the base plate 380' will, in many aspects, be similar to the use of system 300 described above, with the addition of the electromagnetic source 370' directed at the thermal structures 384' in the base plate 380'. The energy provided by the electromagnetic energy source 370' may be controlled to obtain the desired temperatures in the process chambers (by, e.g. varying the power output of the source 370', providing a shutter system, etc.).

The heating of process chambers using thermal structures 384' in base plate 380' may be performed in connection with heating using an electromagnetic energy source located above the device 310' to provide even faster heating and/or more uniform temperature distribution of the process chambers in the device 310'. In such a system and method, electromagnetic radiation may be delivered directly to the process chambers (referring to the system and method depicted in FIG. 9) while the process chambers are simultaneously being heated by thermal energy conduction from below using thermal structures 384'. In another alternative, the process chambers in the device 310' may be heated using only the thermal structures 384', i.e., without the need to direct any electromagnetic energy directly into the process chambers using, e.g., an electromagnetic energy source 370 located above the device 310'.

Figure 9C:
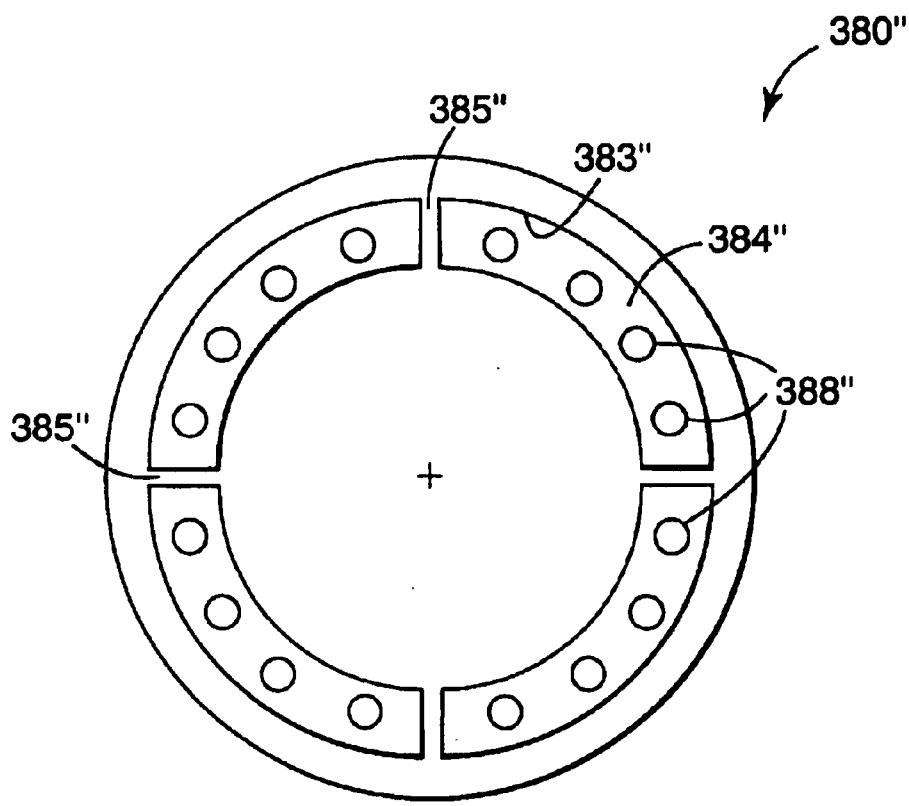
FIG. 9C is a plan view of an alternative base plate for a thermal processing system according to the present invention.

In yet another variation depicted in FIG. 9C, the bottom of a base plate 380" is depicted. A series of openings 383" are provided in the bottom of the base plate 380" with the openings 383" being separated by struts 385". The bottom surface of a thermal structure 384" is exposed within the openings 383" such that electromagnetic energy directed at the thermal structure 384" can be absorbed and converted to thermal energy as described above.

Also seen in FIG. 9C are thermoelectric modules 388" either attached to or embedded within the thermal structure 384". The thermoelectric modules 388" may be provided in the form of, e.g., Peltier elements, resistive heaters, etc. Although a number of thermoelectric modules 388" are depicted, a single thermoelectric module may alternatively be provided.

With the base plate 380", control over the temperature of the thermal structures 384' may be effected by controlling the temperature of the thermoelectric modules 388" alone or in combination with electromagnetic energy directed at the bottom surface of the thermal structures 384'. Where the temperature of the thermal structure 384" is to be controlled by controlling the temperature of the thermoelectric modules 388" alone (i.e., where the thermal structure 384" is not to be heated by converting electromagnetic energy directed at the bottom surface of the thermal structure 384" to thermal energy), the materials selected for manufacturing the thermal structure 384" may be chosen based on their thermal conductivity, with no consideration given for the ability of the materials to absorb electromagnetic energy. Suitable materials may include but are not limited to, e.g., metals (such as, e.g., aluminum, gold, copper, etc.).

By combining the thermoelectric modules 388" with the thermal structure 384" advantages may be obtained in the form of improved temperature uniformity as the thermal structure 384" serves as a sink to equilibrate variations in the operating characteristics of the individual thermoelectric modules 388".

The thermoelectric modules 388" provide another option in controlling the temperature of sample materials in the process chambers of device located above the thermal structure 384". The thermoelectric modules 388" may be used in addition to directing electromagnetic energy into the process chambers and directing electromagnetic energy at the thermal structure 384" to provide three heat sources. Alternatively, the thermoelectric modules 388" may be used alone to heat the process chambers on a device located above the base plate 380" or they may be used in connection with the delivery of electromagnetic energy directly into the process chambers of the device (in the absence of electromagnetic energy directed at the bottom surface of the thermal structure 384".

The net result is a system having the ability to provide electromagnetic energy directly into the process chambers, thermal structures that can convert impinging electromagnetic energy into thermal energy for conduction to the process chambers in a device, and thermoelectric modules whose temperature can be controlled to control the temperature of the thermal structures (and, in turn, any process chambers in thermal communication with the thermal structures). As a result, temperature control over sample materials within the process chambers of a device located on the base plate may be effected in a variety of manners.

Figure 10:
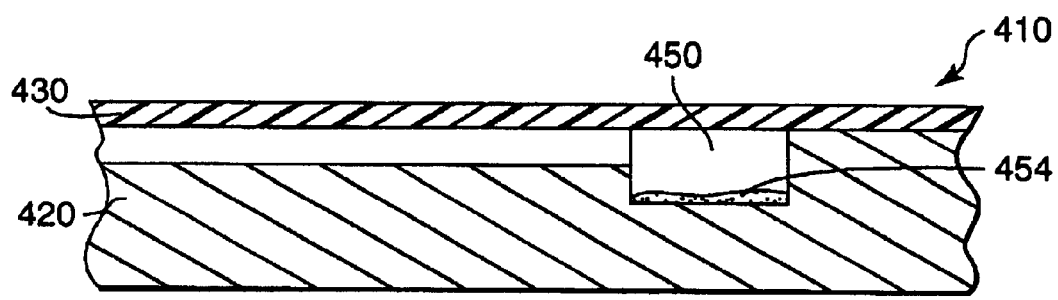
FIG. 10 is partial cross-sectional view of another device according to the present invention.

Referring now to FIG. 10, which depicts a partial cross-sectional view of an alternative device 410 according to the present invention, temperature sensing materials 454 may be located within the process chambers 450 of the device 410. Among the potential temperature sensing materials 454 are structures that incorporate thermochromic dyes, temperature-sensitive fluorescent materials, liquid crystal materials with a colorimetric phase transition, etc. It may be desirable that these materials be in direct contact with any sample materials in the process chambers 450 and, in the illustrated embodiment, the temperature sensing material 454 surrounds at least a portion of the process chamber 450. Many other structures and techniques for providing such temperature sensing materials 454 may, however, be substituted for that illustrated in FIG. 10. For example a portion of the substrate 420 or the first layer 430 may be doped or coated with a temperature sensing material.

Figure 10A:
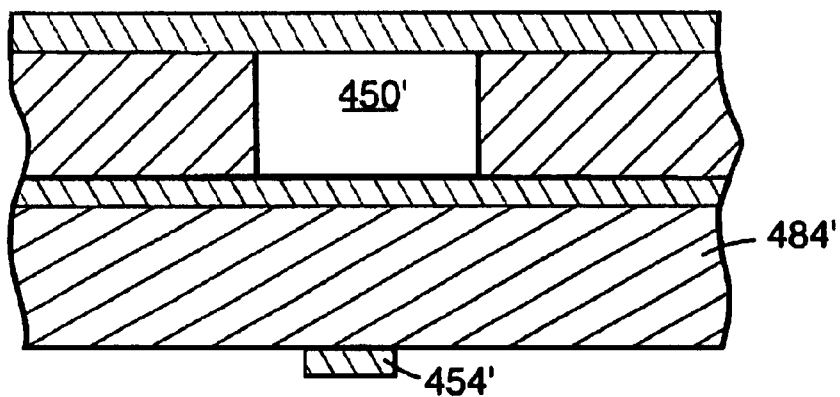
FIG. 10A depicts one device according to the present invention that includes temperature sensing material on the device.

The use of another potential temperature sensing material is depicted in FIG. 10A, where liquid crystal materials (in this example provided in the form of a film) are provided to supply temperature feedback information. Some liquid crystal materials are available that have relatively narrow colorimetric phase transition windows of, e.g., 2 degrees Centigrade. Such narrow transition window temperature sensors could be used, e.g., to monitor selected low and high temperatures in a thermal processing system. Other liquid crystal materials with broader transition windows may be monitored for their color change in between the upper and lower limit indicators. One potential advantage of liquid crystal materials is that their exhibited color changes can be monitored remotely, i.e., without contacting the material, by, e.g., detecting the color changes using a spectrophotometer.

Films incorporating liquid crystal materials could be located in contact with the sample materials in a process chamber as discussed above with respect to FIG. 10 (see reference no. 454). In another alternative depicted in FIG. 10A, the liquid crystal film 454' is located on a thermal structure 484' that is located below the process chamber 450' (where the thermal structure 484' is, e.g., similar in construction to those described above in connection with FIGS. 9A–9C). In such a system, the film 454' could be used to verify the accuracy of a non-contact temperature servo-control system controlling the delivery of electromagnetic energy to the thermal structure 484'. For example, a low temperature indicator could be used to monitor the selected low temperature (e.g., about 50° C. to about 52° C.), a high temperature indicator could be used to monitor the selected high temperature (e.g., about 94° C. to about 96° C.), and a broad range indicator (e.g., about 50° C. to about 100° C.) could be used to monitor the temperature of the thermal structure 484' in between the selected low and high temperatures. One alternative to a broad range indicator could be a series of narrower indicators interspersed between the low and high temperature indicators.

The liquid crystal film temperature indicators could be used a sole source of temperature feedback, or they could be used to verify the accuracy and otherwise calibrate other temperature sensors, such as, e.g., the thermocouples described above.

Figure 11:
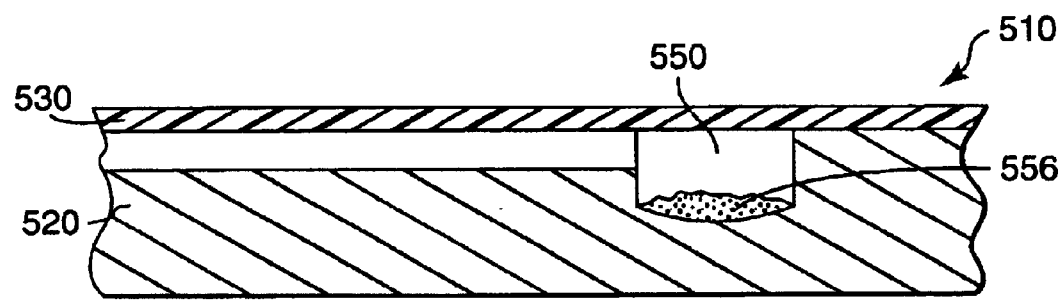
FIG. 11 is a partial cross-sectional view of another device according to the present invention.

FIG. 11 illustrates another device 510 (in a partial cross-sectional view) according to the present invention in which electromagnetic energy receptive materials 556 are located proximate the process chambers 550. It may be desirable that the electromagnetic energy receptive materials 556 be in direct contact with any sample materials in the process chambers 550 and, in the illustrated embodiment, the electromagnetic energy receptive materials 556 surround at least a portion of the process chamber 550. Many other structures and techniques for providing electromagnetic energy receptive materials 556 may, however, be substituted for that illustrated in FIG. 11. For example a portion of the substrate 520 or the first layer 530 may be coated with an electromagnetic energy receptive material.

The electromagnetic energy receptive material 556 can take a variety of forms, provided that is capable of converting electromagnetic radiation in one form or another to thermal energy. That thermal energy can then be communicated to the sample materials in the process chambers 550 by, e.g., conduction. Examples of some suitable materials may include those described in U.S. Pat. No. 5,278,377 (Tsai); U.S. Pat. No. 5,446,270 (Chamberlain et al.); U.S. Pat. No. 5,529,708 (Palmgren et al.); and U.S. Pat. No. 5,925,455 (Bruzzone et al.). Thermal processes using electromagnetic energy absorptive materials are described in, e.g., U.S. Pat. No. 5,721,123 (Hayes et al.).

The advantage of using an electromagnetic energy receptive material 556 is that the sample materials in the device 510 can be heated in the absence of physical contact with the device 510. For example, if the electromagnetic energy receptive material 556 is sensitive to radio-frequency (RF) radiation, the device 510 can be rotated such that the process chambers 550 are resident within an RF field for sufficient time to obtain the desired heating. Similar non-contact heating may be obtained with microwave radiation, etc. It will, however, be understood that the form in which the electromagnetic radiation is provided should be compatible with the sample materials located within the process chambers 550.

Electromagnetic energy receptive materials may include, e.g., absorbers that absorb light in the visible, near-infrared (NIR) and far-infrared region such as dye molecules, carbon dispersions, diamond-like carbon, conducting polymers such as polypyrrole. Absorbers could be made in the form of films coated on the walls of the structure, could be incorporated within microcapsules, could be coated on the surface of beads or in the form of foams, or in a structure that has thermal proximity by a coating of such material on the exterior of the chamber, the intervening materials between the chamber being thermally conducting.

Polycarbonate films, for example, impregnated with an NIR dye or other absorber can be prepared by solvent casting. These films could be incorporated into the device either by bonding to the process chamber, or by in situ casting of the film in the process chamber. Another potential embodiment is to use encapsulated absorbing molecules in a matrix such as, but not limited to, microcapsules, hollow beads, etc., made of polymeric organic or inorganic materials.

Carbon-based systems can also be used as films, for example diamond-like carbon (DLC). DLC can be deposited by a plasma assisted chemical vapor deposition onto a substrate like polycarbonate. Process chambers could, e.g., be coated with DLC films by a masked procedure to, e.g., produce patterned DLC films.

Figure 12:
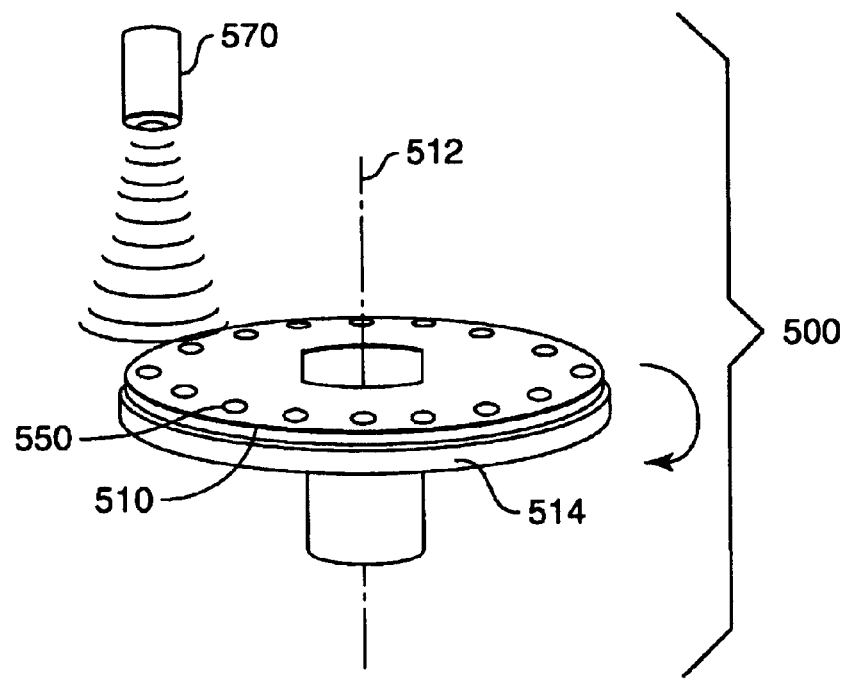
FIG. 12 is a schematic diagram of another thermal processing system according to the present invention.

FIG. 12 schematically illustrates another system 500 in which device 510 is located on a spindle 514 that rotates the device about an axis 512. The device 510 includes process chambers 550 into which a sample material is distributed by, e.g., distribution channels as discussed above or any other suitable techniques and/or structures.

After distribution of the sample material into the process chambers, individual chambers 550 can be selectively heated by suitable electromagnetic energy, e.g., RF, microwave, etc., supplied by an electromagnetic energy source 570 to heat electromagnetic energy receptive materials in the device 510. The electromagnetic energy receptive materials can then communicate the thermal energy to sample materials in the process chambers 550. The electromagnetic energy source 570 may be provided continuously or intermittently as discussed above with respect to the system 300 above. Various cooling and detection mechanisms such as those discussed in connection with system 300 (see FIG. 9) may also be incorporated into system 500.

FIGS. 13–16 illustrate another embodiment of a device in accord with the present invention. Portions of the device 610 are depicted in a variety of plan and partial cross-sectional views. Generally, the device 610 may preferably be in the form of a disc similar to that seen in, e.g., FIG. 1. The device 610 includes a core 620 in which a variety of structures are formed. A first cover layer 630 is attached to a first major side 622 of the core 620 and a second cover layer 640 is attached to a second major side 624 of the core 620. FIGS. 13–16 illustrate one set of interconnected process chambers and other features that may be replicated a number of times around the device 610 in a manner similar to the process chambers 50 arrayed about device 10 in FIG. 1. Each set of interconnected process chambers and other features can be described as forming a process chamber array, with a number of the process chamber arrays arranged generally radially about the device 610.

Figure 13:
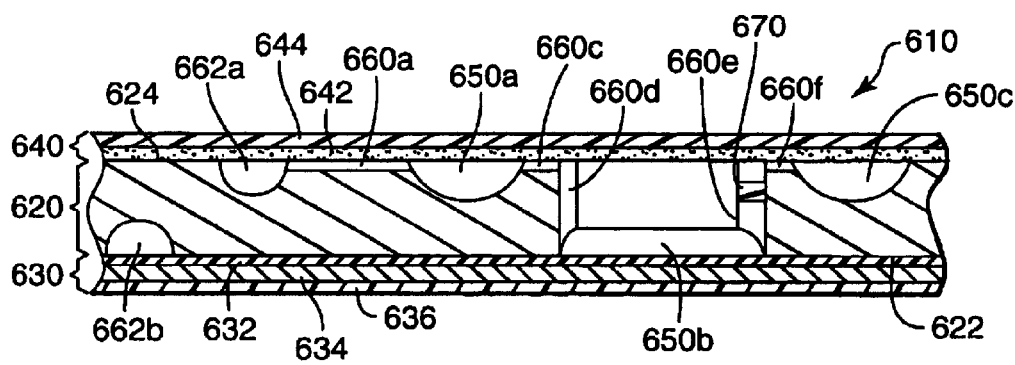
FIG. 13 is a partial cross-sectional view of another device according to the present invention taken along line 13—13 in FIG. 14.
Figure 14:
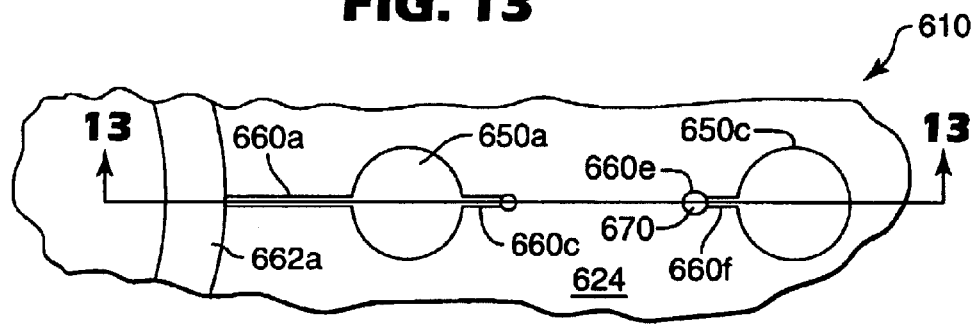
FIG. 14 is a plan view of one surface of a device according to the present invention.
Figure 15:
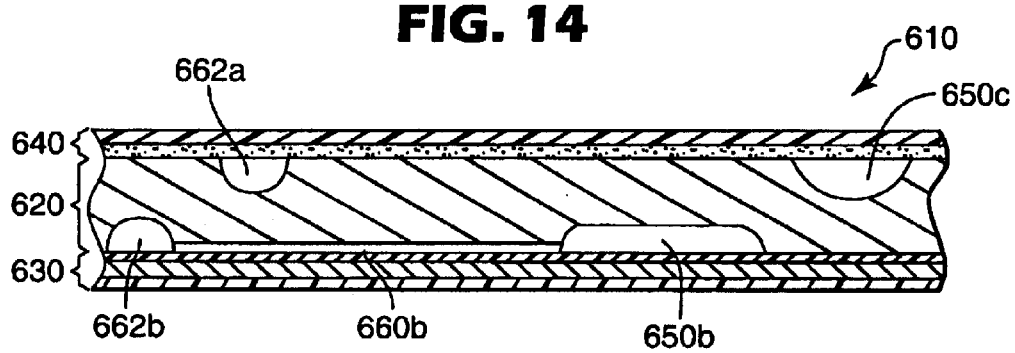
FIG. 15 is a partial cross-sectional view of the device of FIGS. 13 and 14 taken along line 15—15 in FIG. 16.
Figure 16:
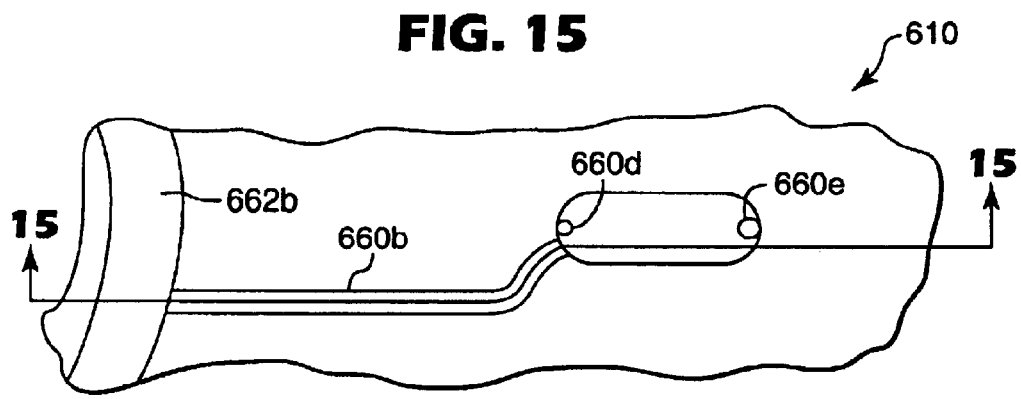
FIG. 16 is a plan view of another surface of the device of FIGS. 13–15.

FIG. 13 is a partial cross-sectional view of a portion of the device 610 including one of the process chamber arrays that is taken along line 13—13 in FIG. 14, which is a plan view of the second major side 624 of the core 620 with the second cover layer 640 removed. FIG. 15 is a partial cross-sectional view of a portion of the device 610 taken along line 15—15 in FIG. 16, which is a plan view of the first major side 622 of the core 620 with the first cover layer 640 removed.

The first cover layer 630 may include multiple sub-layers 632, 634, and 636 in the various constructions described above. It may be preferred that the first cover layer 630 include a reflective sub-layer (e.g., metallic, polymeric, etc.) as discussed in the embodiments described above. The second cover layer 640 may include, e.g., an adhesive 642 and a substrate 644, both of which may be optically clear or otherwise transmissive to electromagnetic energy of selected wavelengths.

Among the features formed in the core 620 are a loading chamber 662a that, in the illustrated embodiment, is in the form of an annular ring (only a portion of which is seen in FIGS. 13–16). The loading chamber 662a is in fluid communication with a first or inner process chamber 650a through a channel 660a. It will typically be preferred that the loading chamber 662a be located closer to the center of the device 610 than the inner process chamber 650a such that rotation of the device 610 about its center causes materials located in the loading chamber 662a to move towards inner process chamber 650a through channel 660a.

The core 620 also includes features formed in the first major surface 622, such as intermediate process chamber 650b, which may be another chamber in which materials are thermally processed. Alternatively, the intermediate process chamber 650b may be provided to perform another function, e.g., filter materials delivered to it from inner process chamber 650a. The intermediate process chamber 650b may be in fluid communication with a second loading chamber 662b through channel 660b that, in the illustrated embodiment, is formed in the first major surface 622 of the core 620.

The inner process chamber 650a and intermediate process chamber 650b are connected by a channel 660c and a via 660d. The channel 660c extends from the inner process chamber 650a to the via 660d which, in turn, extends to the intermediate process chamber 650b. The channel 660c and/or via 660d may preferably include a valve structure located between the process chambers if precise control over the movement of materials between the inner process chamber 650a and intermediate process chamber 650b is desired. The valve structure may take a number of forms, e.g., thermal plugs (e.g., waxes, etc.) or other structures that can be opened when desired. Alternatively, the valving may be provided by varying the rotational speed of the disc to overcome the resistance of materials to move through the channel 660c and/or via 660d.

The intermediate process chamber 650b is also connected to the outer process chamber 650c by a via 660e and channel 660f in a manner similar to that used to connect inner process chamber 650a and intermediate process chamber 650b. The via 660e and/or channel 660f may also include a valve structure if so desired.

It is preferred that the process chamber array including chambers 650a, 650b, and 650c be arranged generally radially from the center of the device 610, i.e., the point about which the device is rotated. As a result, rotation of the device 610 can be used to move materials successively from inner process chamber 650a to intermediate process chamber 650b and, finally, to outer process chamber 650c. By moving the materials through the process chambers as desired, selected processes can be performed sequentially within the process chamber array on the device 610.

It may be desired that the channels and vias in the device 610 may also include filters or other structures/materials needed to perform functions. For example, a porous capture plug 670 may be located within the via 660e. The porous capture plug 670 may advantageously capture filter materials moving from the loading chamber 662b to the intermediate process chamber 650b. For example, it may be desirable to dispense filtering material in the form of, e.g., beaded size exclusion substances. Such materials may be entrained within a fluid when supplied to the loading chamber 662b. When the device 610 is rotated, the entrained beads may be driven to the intermediate process chamber 650b through channel 660b. The porous capture plug 670 in via 660e allows the fluid carrying the beads to pass but prevents the beads from passing, thereby capturing them within the process chamber 650b.

A particular advantage of the porous capture plug 670 used to capture filtering material within process chamber 650b is that the filter material dispensed to the chamber 650b may be selected at the point-of-use based on the characteristics of the sample materials being processed. Where the filtering material dispensed to the chamber 650b is, e.g., size exclusion beads, the properties of the beads may be selected to, e.g., remove the typically shorter PCR primers while allowing the typically longer PCR products to pass through to the outer process chamber 650c. The sizes of the primers and the PCR products may vary in each application and the ability to select the appropriate size exclusion material for process chamber 650b may be particularly advantageous.

Device of the present invention with process chamber arrays such as those illustrated in, e.g., FIGS. 13–16, may be used to provide integrated processing of starting sample materials by, e.g., amplification of a starting sample material within a process chamber array on a device. Each of the process chamber arrays include a number of chambers that are preferably arranged generally radially on a device (such that centrifugal forces can move fluids sequentially from chamber to chamber). The chambers within each of the arrays are in fluid communication using channels or other conduits that may, in some embodiments, include valve structures to control the movement as desired.

Figure 17:
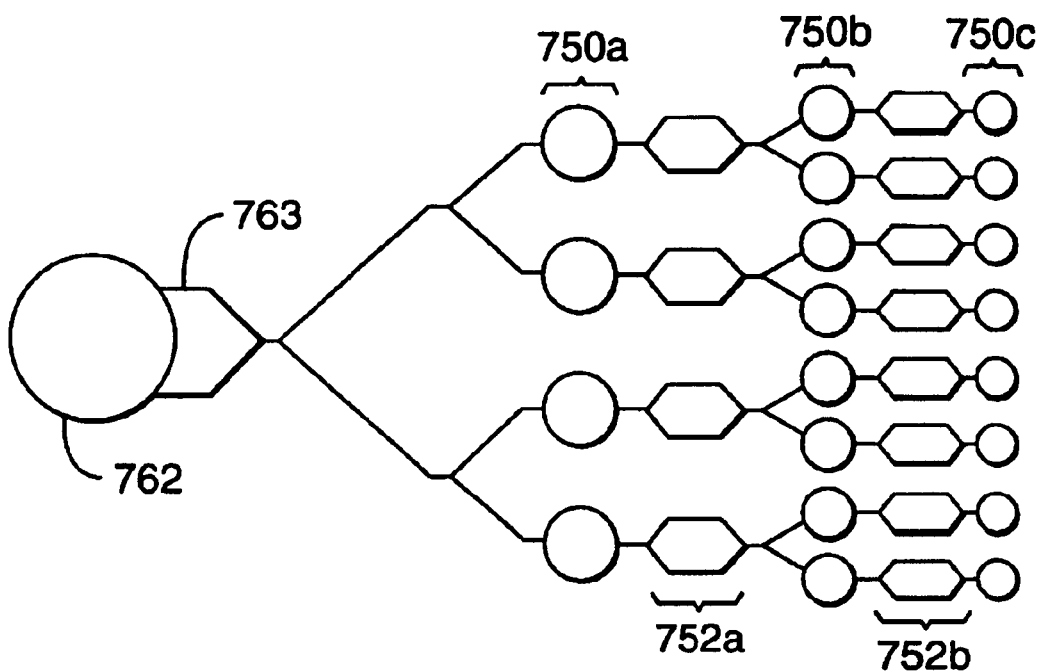
FIG. 17 is a schematic diagram of one structure that may be used to provide integrated processing of starting sample materials by, e.g., PCR amplification and Sanger sequencing on a single device.

One example of an integrated process that can be performed in a process chamber array is schematically illustrated in FIG. 17 where a loading chamber 762 is provided to receive, e.g., a starting sample material. The array and one illustrative method of using the array will be described below. The illustrative method involves PCR amplification, followed by Sanger sequencing to obtain a desired end product. This combination of processes is, however, intended to be illustrative only and should not be construed as limiting the present invention.

Starting sample material, e.g., lysed blood cells, is provided in the chamber 762. A filter 763 is preferably provided to filter the starting sample material as it moves from the loading chamber 762 to the first process chambers 750a. The filter 763 is, however, optional and may not be required depending on the properties of the starting sample material.

The first process chambers 750a may preferably include suitable PCR primers as supplied, e.g., dried down in each of the chambers 750a. Each of the chambers 750a may include the same primer or different primers depending on the nature of the investigation being performed on the starting sample material. One alternative to providing the primers in the process chambers 750a before loading the sample is to add a suitable primer to the loading chamber 762 with the starting sample material (provided that the primer is capable of passing through the filter 763, if present).

After locating the starting sample material and any required primers in the process chambers 750a, the materials in the process chambers 750a are thermally cycled under conditions suitable for PCR amplification of the selected genetic material.

After completion of the PCR amplification process, the materials in each of the first process chambers 750a may be moved through another filter chamber 752a (one filter chamber 752a for each process chamber 750a) to remove unwanted materials from the amplified materials, e.g., PCR primers, unwanted materials in the starting sample that were not removed by filter 763, etc. The filter chambers 752a may, for example, contain size exclusion substances, such as permeation gels, beads, etc. (e.g., MicroSpin or Sephadex available from Amersham Pharmacia Biotech AB, Uppsala, Sweden).

After clean-up of the sample materials in the filter chambers 752a, the filtered PCR amplification products from each of the first process chambers 750a are moved into a pair of multiplexed second process chambers 750b for, e.g., Sanger sequencing of the genetic materials amplified in the first process chambers 750a through appropriate control of the thermal conditions encountered in second process chambers 750b.

After the desired processing has been performed in the second process chambers 750b, the processed material (Sanger sequenced sample material if that is the process performed in the process chambers 750b) is moved from each of the process chambers 750b through another set of filter chambers 752b to remove, e.g., dyes or other unwanted materials from the product of the second process chambers 750b. The filtered product is then moved from the filter chambers 752b into output chambers 750c where it can be removed.

As with the process chamber arrays illustrated in FIGS. 13–16, it is also preferred that process chamber arrays such as the array illustrated in FIG. 17 be arranged generally radially on a device such that rotation of the device will move materials from the loading chamber 762 towards the output chambers 750c. More preferably, it is preferred that two or more of the process chamber arrays illustrated in FIG. 17 be arranged on a single device, with the loading chambers 762 of each array located closest to the axis of rotation such that the materials can be moved through the array by centrifugal forces developed during rotation. Alternatively, the arrays may be located on a device that is held in a manner that allows rotation of device containing the array such that centrifugal forces move the materials from the loading chamber 762 towards the output chambers 750c. Loading of sample materials into process chambers using centrifugal force is also described, for example, in U.S. patent application Ser. No. 09/710,184 filed on Nov. 10, 2000 and titled CENTRIFUGAL FILLING OF SAMPLE PROCESSING DEVICES.

A variety of advantages of the integrated process chamber array illustrated in FIG. 17 stem from the ability to move from a raw starting sample material to an isolated sequenced product in a single device. Among those advantages are reductions in the number physical transfers (by pipetting, etc.) that can be problematic when working with small volumes of materials. Another advantage is that multiple parallel processes can be simultaneously performed, providing potential improvements in confidence levels regarding the accuracy of the process results. In addition, there may be an enhanced level of control in ensuring that the process chambers see the same conditions with respect to, e.g., thermal cycling, etc.

Figure 18:
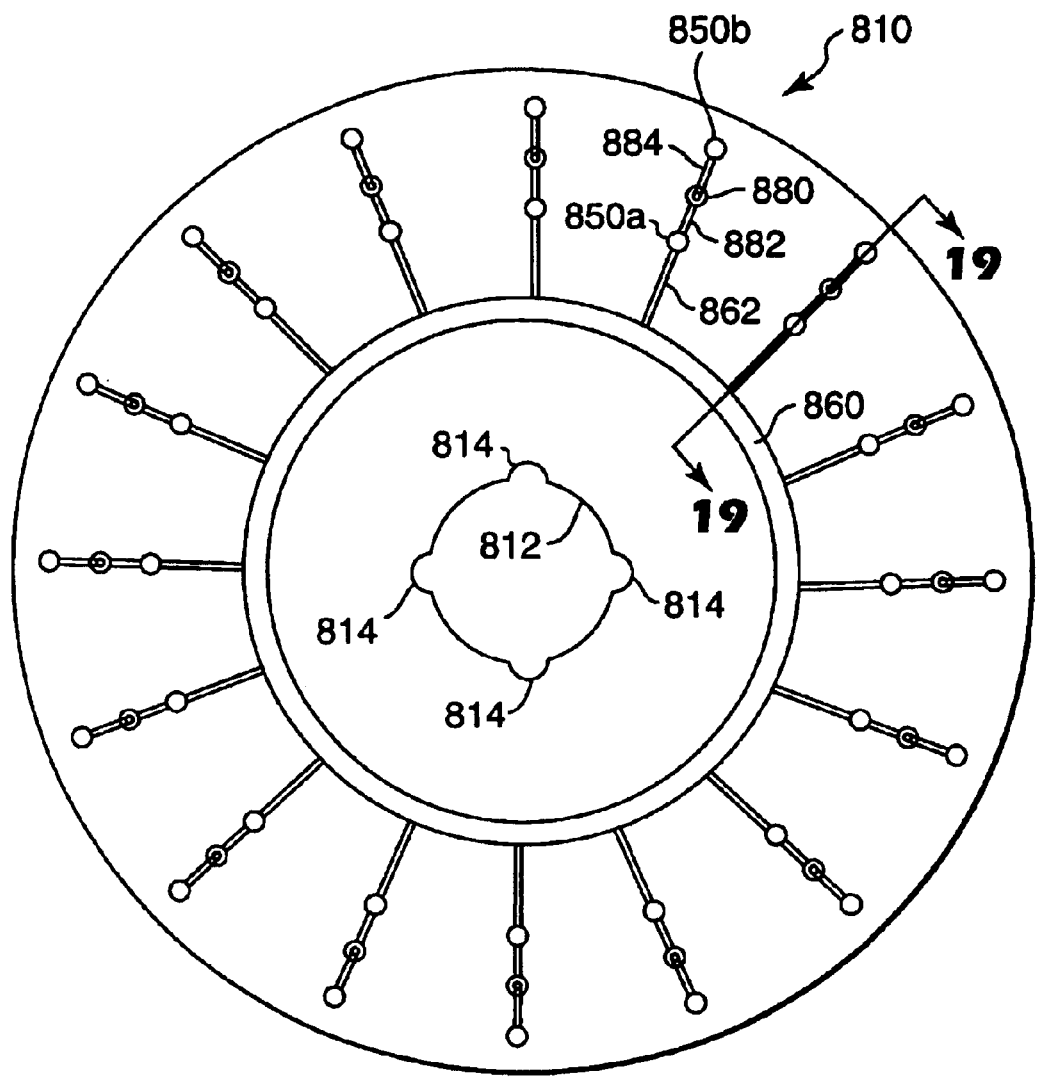
FIG. 18 is a plan view of one major surface of a device according to the present invention.
Figure 19:
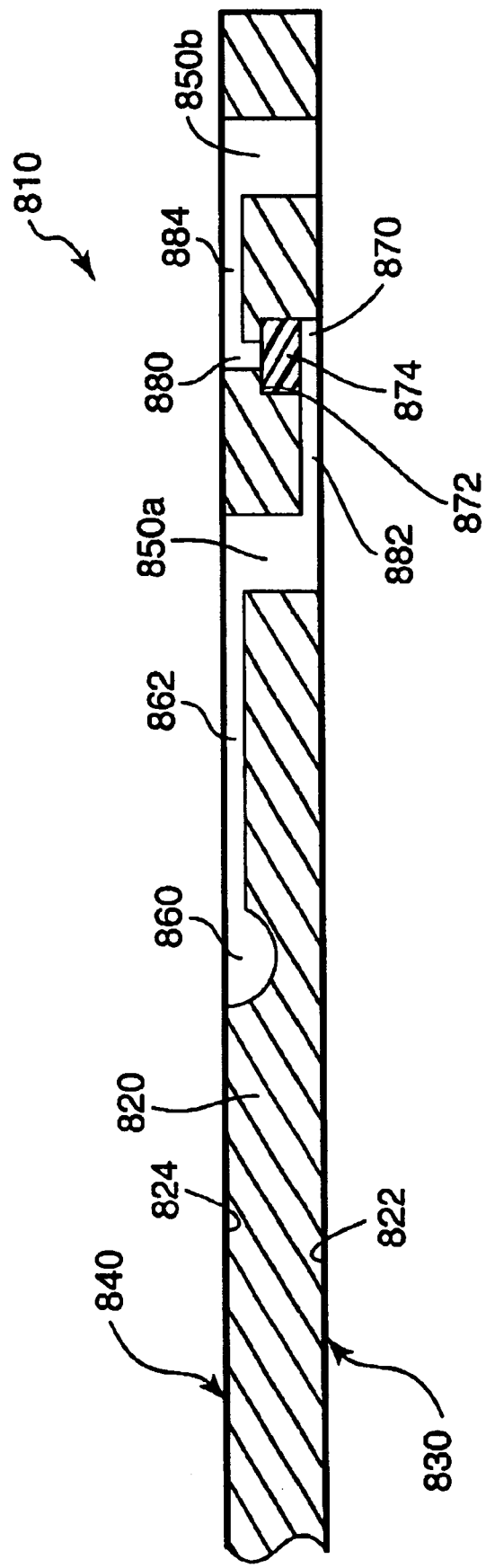
FIG. 19 is a cross-sectional view of the device of FIG. 18 taken along line 19—19 in FIG. 18.
Figure 20:
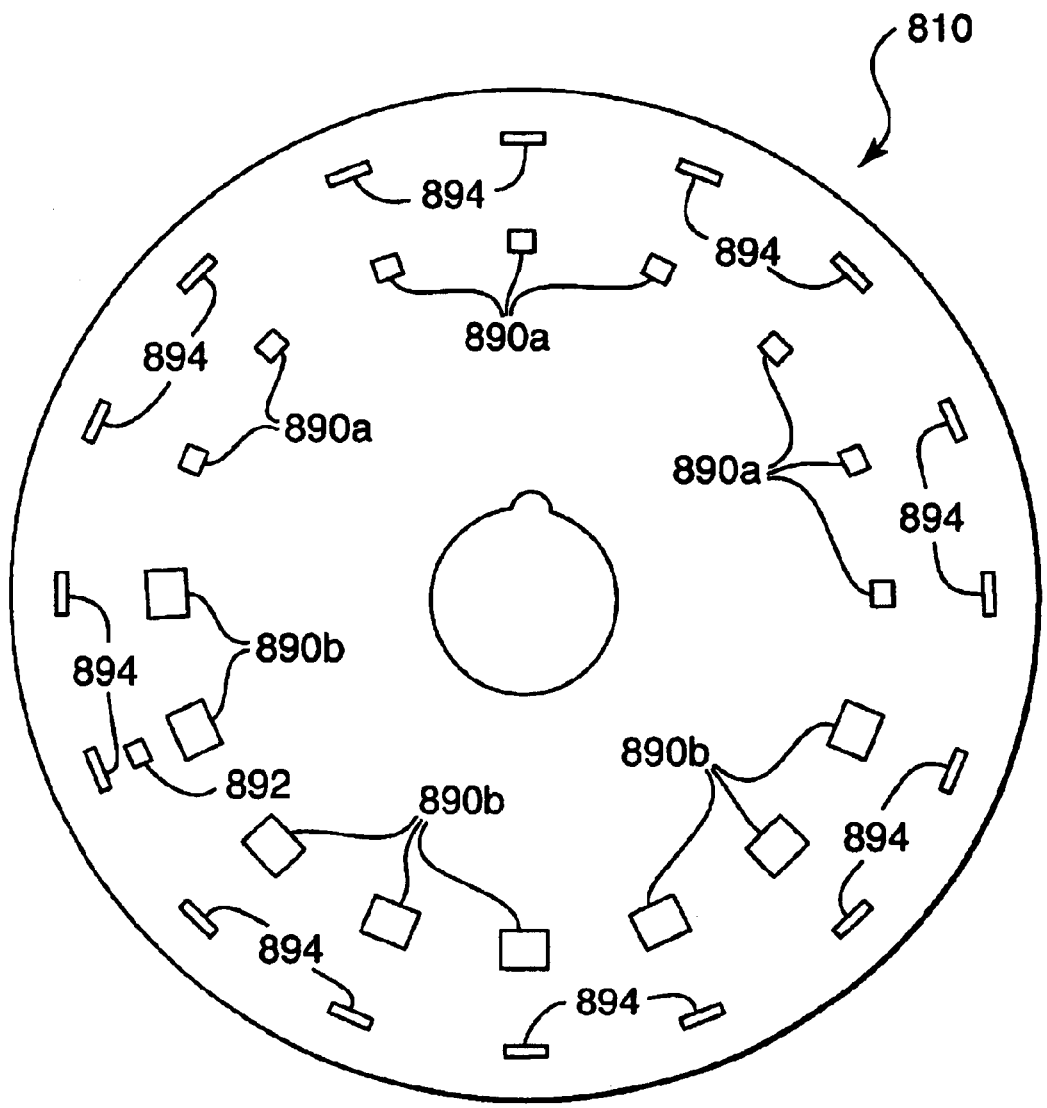
FIG. 20 is a plan view of the other major surface of the device of FIG. 18, depicting a control pattern provided on the device.

FIGS. 18–20 illustrate another embodiment of a device and methods according to the present invention incorporating valves separating the process chambers within each process chamber array. The illustrated device 810 includes a plurality of process chamber arrays in a manner similar to that described with respect to the embodiment illustrated in FIGS. 13–16 above. One of the process chamber arrays is depicted in the enlarged cross-sectional view of FIG. 19.

The device 810 includes a first cover layer 830 attached to a first major side 822 of the substrate 820 and a second cover layer 840 attached to a second major side 824 of the substrate 820. The substrate 820 and cover layers 830 and 840 may be attached by any suitable technique or techniques, including, but not limited to, adhesives, welding (chemical and/or thermal), etc.

The device 810 also illustrates one embodiment of a registration system as discussed above in the form of a number of key slots 814 formed about the periphery of the opening 812 in the center of the device 810. The key slots 814 can cooperate with complementary structures formed on, e.g., a spindle, used to rotate the device 810. The key slots 814 can, thus, be used to maintain the rotational position of the device 810 on such a spindle. Although multiple key slots 814 are shown, it will be understood that only one such slot 814 may be required to fix the rotational position of the device 810 on a spindle.

The first cover layer 830 may be homogeneous or it may include multiple sub-layers as described above. It may be preferred that the first cover layer 830 be reflective for electromagnetic energy of selected wavelengths as described above. The second cover layer 840 may include, e.g., an adhesive on a carrier layer, both of which may be optically clear or otherwise transmissive to electromagnetic energy of selected wavelengths.

Among the features formed in the substrate 820 are a loading chamber 860 that, in the illustrated embodiment, is in the form of an annular ring. Each of the process chamber arrays also include inner or first process chambers 850a and outer or second process chambers 850b located further out radially from a center of the device 810.

The loading chamber 860 is in fluid communication with the inner process chamber 850a through channel 862. As a result, rotation of the device 810 about its center will force sample material to move from the loading chamber 860 into the first process chamber 850a where the first thermal processing of the sample material may be performed.

The device 810 also includes a valve 870 located between and separating the inner and outer process chambers 850a and 850b. The valve 870 is normally closed when the device 810 is supplied to a user to prevent movement of the sample material from the first process chamber 850a into the second process chamber 850b.

The valve 870 may preferably be located within a via 880 that is in fluid communication with inner process chamber 850a through channel 882 on one side and in fluid communication with the outer process chamber 850b through channel 884 on the opposite side. It may be preferred that the via 880 be formed such that it extends between the first and second major surfaces 822 and 824 of the substrate 820 as depicted.

The valve 870 includes an impermeable barrier 872 that prevents fluids from moving between the process chambers 850a and 850b when it is intact. The impermeable barrier 872 may preferably be distinct from the substrate 820, i.e., it is preferably made of a material that is different than the material used for the substrate 820. By using different materials for the substrate 820 and the impermeable barrier 872, each material can be selected for its desired characteristics. Alternatively, the impermeable barrier may be integral with the substrate 820, i.e., made of the same material as the substrate 820. For example, the impermeable barrier may simply be molded into the substrate 820. If so, it may be coated or impregnated to enhance its ability to absorb electromagnetic energy.

The impermeable barrier 872 may be made of any suitable material, although it may be preferred that the material of the barrier 872 form voids without the production of any significant byproducts, waste, etc. that could interfere with the reactions or processes taking place in process chambers. A preferred class of materials are pigmented oriented polymeric films, such as, for example, films used to manufacture commercially available can liners or bags. A suitable film may be a black can liner, 1.18 mils thick, available from Himolene Incorporated, of Danbury, Conn. under the designation 406230E.

It may further be preferred that the impermeable barrier 872 of the valve 870 include material susceptible of absorbing electromagnetic energy of selected wavelengths and converting that energy to heat, resulting in the formation of a void in the impermeable barrier 872. The absorptive material may be contained within the impermeable barrier 872 or coated on a surface thereof.

The valve 870 illustrated in FIG. 19 also includes an optional permeable support 874 located proximate at least one side of the impermeable barrier 872. The support 874 is permeable to the fluids moving between the process chambers 850a and 850b, although it may perform some filtering functions in addition to supporting the impermeable barrier 872. It may be preferred that the support 874 be somewhat resilient to assist in sealing the valve 870 by forcing the impermeable barrier 872 against the surfaces in the via 880 with sufficient force to prevent fluid passage in ordinary use of the device 810.

It may be preferred that the support 874 be provided in the form of a porous material as illustrated in FIG. 19. The porous support 874 may preferably be coextensive with the impermeable barrier 872 used in the valve 870. Alternative forms of the support may include rings, sleeves, or any other structure or material that can support at least a portion of the impermeable barrier 872 in the valve 870.

In some embodiments, it may be desirable that the porous support 874 reflect electromagnetic energy of selected wavelengths to assist in the opening of the valve 870 and/or prevent the electromagnetic energy from reaching any underlying fluids, sample materials, etc.

It may be preferred that the porous support 874 be hydrophobic to reduce or prevent fluid contact with the impermeable barrier 872. Alternatively, it may be preferred that the porous support 874 be hydrophilic to promote fluid contact with the impermeable barrier 872 of the valve 870.

Examples of suitable materials for a porous support may include, but are not limited to, porous plugs or membranes, including sintered polypropylene and sintered polyethylene plugs or membranes, e.g., such as those commercially available from Porex Corporation, Fairburn, Ga. The impermeable barrier 872 can also be directly bonded into position (e.g., by a pressure sensitive adhesive, silicone adhesive, epoxy adhesive, thermal welding, etc.) without the need for a support structure.

The valve 870 is opened by forming a void in the impermeable barrier 872. The void may be formed by electromagnetic energy of any suitable wavelength. It may be preferred that laser energy of a suitable wavelength be used. A potential advantage of using laser energy is that the same laser used to heat the materials in the process chambers may be used to form the voids needed to place the process chambers in fluid communication with each other.

It may further be desirable to place the impermeable barrier 872 of the valve 870 within a via 880 as illustrated in FIG. 19. Locating the impermeable barrier 872 within a via 880 and directing electromagnetic energy of some wavelengths into the via 880 may result in some advantages in that the walls of the via 880 may reflect and/or focus at least some of the electromagnetic energy to assist in formation of the void in the barrier 872.

Figure 19A:
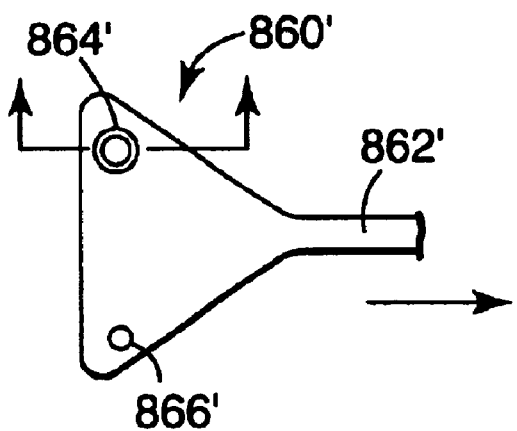
FIG. 19A is a plan view of an alternative loading chamber design for use in connection with the present invention.
Figure 19B:
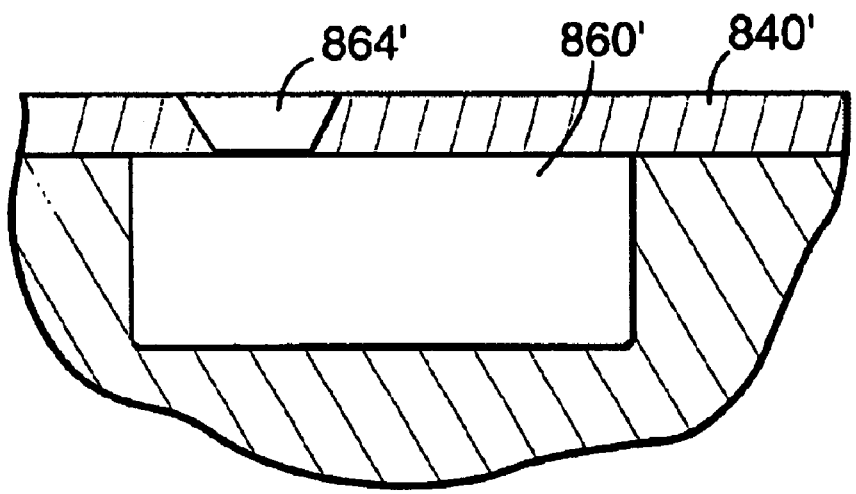
FIG. 19B is an enlarged cross-sectional view of the loading chamber of FIG. 19A taken along line 19B—19B in FIG. 19A.

FIGS. 19A and 19B depict an alternative loading chamber 860' that may be used on connection with one or more of the process chamber arrays of device 810. The loading chamber 860' has a funnel shape that may assist in emptying of the loading chamber as the device 810 is rotated. The wider end of the funnel shaped loading chamber 860' is preferably located closest to the axis of rotation with the loading chamber 860' tapering in the direction of the channel 862' that leads to the first process chamber (not shown in FIG. 19A).

The loading chamber 860' also includes an optional inlet port 864' and an optional vent 866'. These openings are formed in the second cover layer 840'. The inlet port 864' may preferably be tapered to assist in guiding, e.g., a pipette tip, into the volume of the loading chamber 860'. The vent 866' assists in loading of the chamber 860' by providing a opening through which air can escape as the loading chamber 860' is loaded through inlet port 864'.

Advantages of the funnel-shaped loading chamber 860' include control over fluid entry into the system. The shape of the loading chamber 860' can provide for almost 100% filling while reducing or eliminating trapped air. In addition, the shape of the loading chamber 860' may also reduce or prevent premature entry of the sample materials into the channel 862'.

Figure 19C:
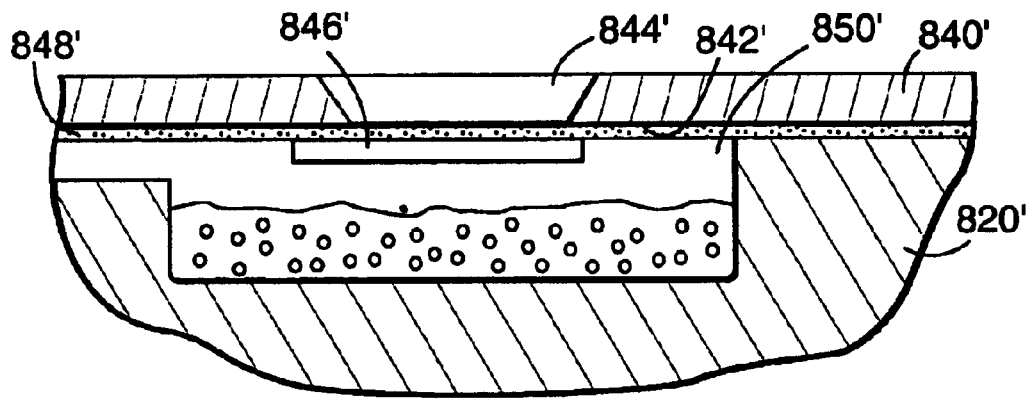
FIG. 19C is a cross-sectional view of a seal system that may be used in connection with the process chambers of the present invention.
Figure 19D:
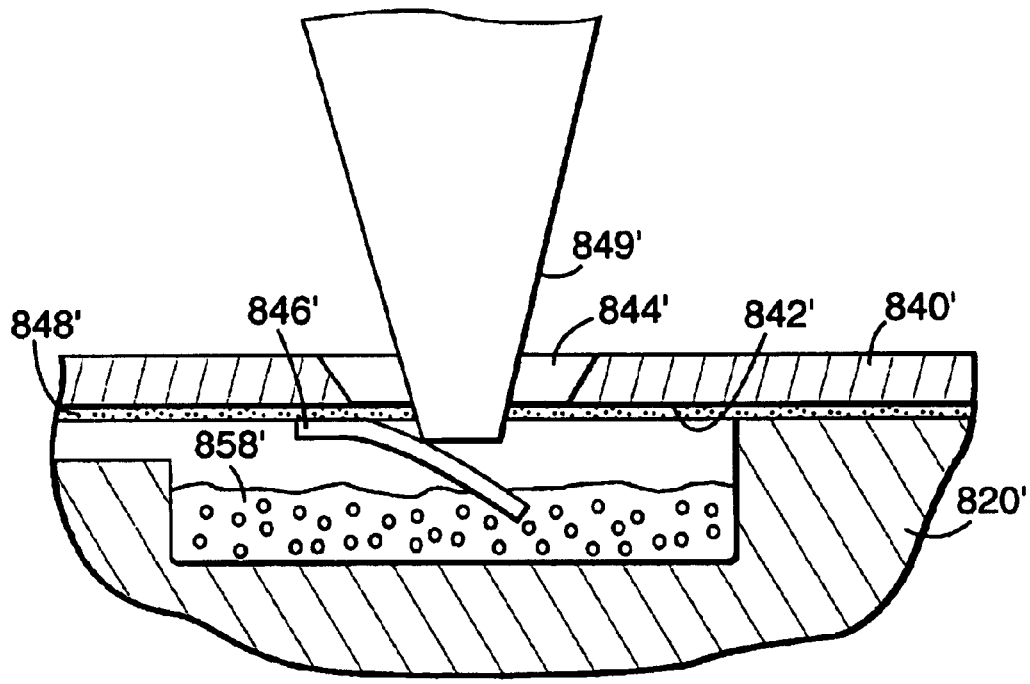
FIG. 19D is a cross-sectional view of a probe accessing the interior of the process chamber through the seal system of FIG. 19C.

FIGS. 19C and 19D depict an optional seal system that may be used in connection with one or more of the process chambers in one or more of the process chamber arrays in the device 810. The seal system includes an opening 844' in the cover layer 840' covering a process chamber 850' formed, at least in part, by a substrate 820'. The opening 844' is closed by a seal 846' that is attached to the inner surface 842' of the cover layer 840' over the opening 844'.

The seal 846' may be attached to the inner surface 842' by any suitable technique, e.g., adhesives, welding, heat sealing, etc. In the depicted embodiment, the seal 846' is attached to the inner surface 842' of the cover layer 840' by adhesive 848'. That adhesive 848' may be used to also attach the cover layer 840' to the substrate 820' as depicted in FIGS. 19C and 19D.

Use of the seal system is depicted in FIG. 19D where the tip of a probe 849' is shown forcing the seal 846' away from attachment to the inner surface 842' of the cover layer 840'. The probe 849' can then access the interior of the process chamber 850' to add to or remove the sample material 858'. Although the probe 849' is depicted as forcing the seal 846'away from only a portion of the cover layer 840', it may completely detach the seal 846' from the cover layer 840'. It may be preferred that the opening 844' in the cover layer 840' be tapered as depicted, e.g., in FIGS. 19C and 19D to assist in guiding the tip of the probe 849' into the process chamber 850'. This guiding feature may be especially helpful for use in connection with robotic unloading systems.

One potential advantage of the seal system is that the probe 849' is not required to cut any components forming the process chamber 850' to access the interior of the process chamber 850'.

The device 810 includes an optional control pattern depicted in FIG. 20 that includes indicators 890a, 890b, 892, and 894 useful in controlling the electromagnetic energy delivered to the process chambers and/or valves. In the illustrated embodiment, the control pattern is located on the first cover layer 830, although other suitable locations may alternatively be used.

The indicators used in the control pattern have at least one characteristic indicative of the electromagnetic energy to be delivered to the associated process chamber and/or valve. The characteristics may include size, shape, color, or any other distinguishing feature that may be detected and used to control the delivery of electromagnetic energy. In the illustrated embodiment, the primary distinguishing characteristics include size and/or shape. It may be preferred that the indicators be detected optically (based on, e.g., contrast with the surrounding surface of the device 810, sensing of a void formed through the device 810, etc.).

The illustrated control pattern includes a first set of indicators 890a associated with some of the inner process chambers 850a and a second set of indicators 890b associated with the rest of the inner process chambers 850a. The difference between the sets of indicators is their size, with the indicators 890a being smaller than the indicators 890b. That size may be used to control the amount of energy delivered to the process chambers associated with each indicator, e.g., the larger indicators 890b may result in the delivery of more energy to their associated process chambers 850a. Alternatively, the differently sized indicators 890a and 890b may be used to control the wavelength of the electromagnetic energy delivered to the associated process chambers 850a (with each of the different indicators denoting a different wavelength of energy). In yet another alternative, both the amount and wavelength of the energy delivered to each process chamber may vary depending on the characteristics of the associated indicators.

One potentially desirable method for using indicators 890a and 890b based on their sizes and the rotation of the device 810 is to begin delivery of electromagnetic energy when the leading edge of the relevant indicator passes a detector and ceasing delivery of that energy when the trailing edge of the same indicator passes the detector. The electromagnetic energy may be controlled at its source by cycling or the delivery may be interrupted by, e.g., a shutter, rotating mirror, or other system.

The indicators 890a and 890b are each associated with only one of the process chambers 850a. Indicator 892, however, is associated with all of the valves 870 on the device 810 and can be used to control the delivery of electromagnetic energy needed to open the valves 870 as described above. In a similar manner, delivery of electromagnetic energy to multiple process chambers 850a could be effected with one indicator in some systems.

Indicators 894 are associated with the outer process chambers 850b and can be used to control delivery of electromagnetic energy to those process chambers. As illustrated, the shape of the indicators 894 is different from the other indicators and those different characteristics may be used for control purposes.

Although the indicators in the illustrated control pattern are located generally in registration with the process chamber or valve with which they are associated, the control pattern need not be so provided. For example, the control pattern may occupy only a portion of the surface of the device 810, e.g., an outer annular ring.

In another alternative, the control pattern or portions thereof may be used to control other components of a system using the device 810. For example, indicators may be provided that control the type of detectors used to monitor the process chambers for, e.g., a desired product, temperature, pH, etc. Such indicators may be provided in the form of bar codes.

Figure 21:
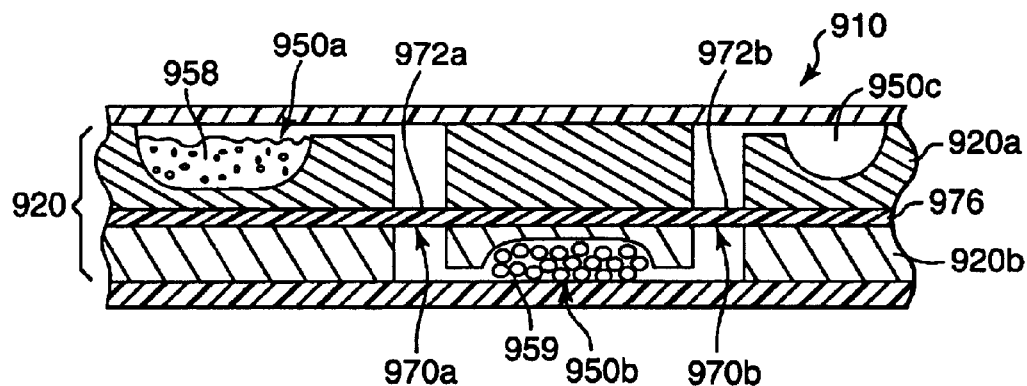
FIG. 21 is a cross-sectional view of another device according to the present invention.
Figure 22:
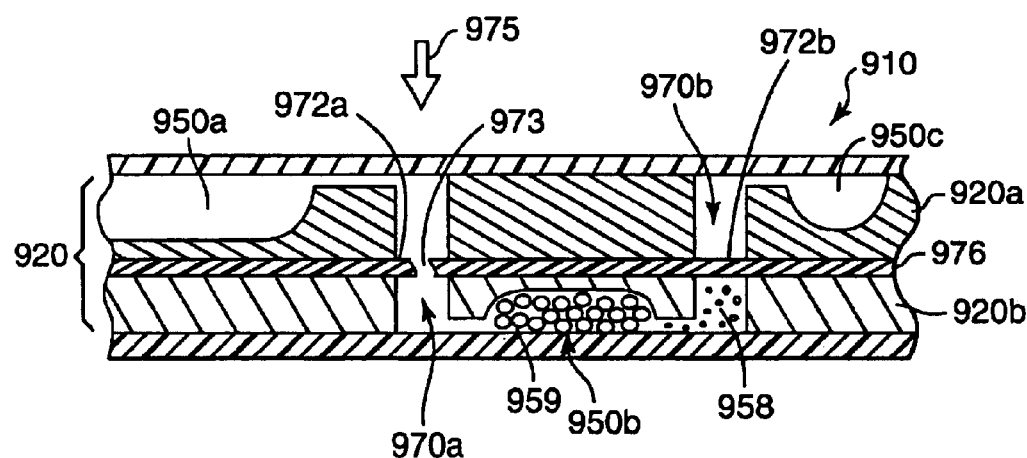
FIG. 22 is a cross-sectional view of the device of FIG. 21 after opening of one of the valves in the device.

FIGS. 21 and 22 illustrate another construction of a device 910. The device is similar in many respects the device 810. One difference, however, is that the substrate 920 includes an upper layer 920a and a lower layer 920b with a valve layer 976 located between the upper layer 920a and lower layer 920b. The valve layer 976 forms the impermeable discs 972a and 972b of the valves 970a and 970b. Unlike the impermeable discs 872 of the valves 870 of the device 810 (which are separate and distinct from each other), the impermeable discs 972a and 97b are formed of portions of the same valve layer 976 which extends between the different valves 970a and 970b.

The layers 920a, 920b and valve layer 976 may be attached together by any suitable technique or combination of techniques. For example, they may be adhesively attached, welded (thermally, chemically, etc.), heat-sealed, etc. It may be desirable that the valve layer 976 be used to form the impermeable discs of all of the valves on the device 910 or only some of the valves. If the valve layer 976 is used to form the impermeable discs of all of the valves, it may be desirable that the valve layer 976 be coextensive with the major surfaces of the device 910. The laminated construction of the device 910 may provide advantages in the manufacturing of the devices 910 by allowing the use of web or other continuous manufacturing processes.

The valves 970a and 970b are used to separate the process chambers 950a, 950b and 950c and control movement of the sample material 958 between the chambers. As illustrated in FIG. 21, the sample material 958 is located in process chamber 950a which is not in fluid communication with process chamber 950b due to the closed state of the valve 970a.

In FIG. 22, however, the impermeable barrier 972a of valve 970a includes a void 973 formed therein after delivery of the appropriate electromagnetic energy 975 into the via 980 containing the valve 970. That void allow the sample material 958 to move into the process chamber 950b from process chamber 950a. In the illustrated embodiment, process chamber 950b includes filter material 959 through which the sample material 958 passes on its way to process chamber 950c.

Such a device could be used in a method of removing ions (e.g., chloride, phosphate) and/or dyes (e.g., dideoxy nucleotide triphosphate dye terminators (ddNTP), fluorescent dyes, near-infrared dyes, visible dyes) from a biological sample material, as well as other devices designed for moving sample materials from one chamber to another. The method includes: providing a device that includes at least two connected process chambers wherein the connection defines at least one volume (e.g., an intermediate process chamber 950b) for containing a solid phase material for removal of ions and/or dyes from a sample material; providing biological sample material in one of the process chambers; transferring the biological sample material from one chamber to another chamber through the connection to allow the biological sample material and solid phase material to remain in contact for a sufficient time to remove at least a portion of the ions and/or dyes from the biological sample material. Optionally, the solid phase material includes two or more different types of particles. Optionally, the connection defines two volumes, each containing a different solid phase material.

Alternative valve constructions that may be used in connection with the devices and methods of the present invention are illustrated in FIGS. 23A, 23B, 24A, 24B, 25A, and 25B. The valves may, for example, be constructed, at least partially, of polymeric materials that exhibit shape memory effects. Some polymers that exhibit shape memory effect are discussed in, e.g., U.S. Pat. No. 5,049,591 (Hayashi et al.); U.S. Pat. No. 5,128,197 (Kobayashi et al.); U.S. Pat. No. 5,135,786 (Hayashi et al.); U.S. Pat. No. 5,139,832 (Hayashi et al.); and U.S. Pat. No. 5,145,935 (Hayashi). Many of these polymers are crosslinked polyurethanes. Other polymers, e.g., polynorbornene, may also exhibit shape memory effects.

In connection with polymeric materials, "shape memory effect" can be generally described as involving the fabrication of a first structure at a temperature above the glass transition temperature ($T_g$) of the polymer. That structure is then cooled below the $T_g$ and deformed into a second structure. When the polymer in the form of the second structure is heated above the $T_g$, the polymer reverts to the first structure.

In addition to exhibiting shape memory effects, any polymeric materials used in connection with the valves should be compatible with the reagents and other materials used in the devices and methods of the present invention. For example, where PCR is to be performed in devices incorporating the shape memory polymer valves, the polymeric materials in the valves are preferably compatible with the materials found in the PCR process.

Turning to FIGS. 23A and 23B, one valve structure that may be useful in connection with the microfluidic devices and methods of the present invention is illustrated. The valve 1070 may be formed in the shape of a cylinder when open as depicted in FIG. 23A and a pinched shape as illustrated in FIG. 23B when closed. The valve 1070 may be constructed to be normally open, i.e., open after manufacturing above the $T_g$ of the polymeric material. As a result, the valve 1070 is closed (FIG. 23B) and then located in a device of the present invention until heated to above the $T_g$ of the shape memory effect polymer. Once heated above the $T_g$ of the polymer, the valve 1070 reverts to its normally open structure (FIG. 23A), thereby allowing materials to pass through the valve 1070. Alternatively, the valve 1070 could be normally closed, such that heating would cause the valve 1070 to move from the open state (FIG. 23A) to the closed state (FIG. 23B).

Heating of the polymer may be achieved by any suitable technique, although it may be preferred to heat the polymer by non-contact heating methods. For example, the valve 1070 may be heated by electromagnetic energy (e.g., laser energy, RF energy, etc.). Alternatively, the polymer may be heated by conduction using resistance heaters, Peltier devices, etc. In another alternative, the valve 1070 may be heated by convection using, e.g., hot air or other heated fluids. Where a laser or other non-contact source of energy is used, the polymeric material used to construct the valve 1070 may be impregnated or otherwise include one or more materials that absorb electromagnetic energy of selected wavelengths. For example, the polymeric material may be impregnated with a dye that absorbs laser energy (e.g., a dye that absorbs near infrared radiation, such as IR 792 perchlorate available from Aldrich Chemical).

Another valve structure 1170 is illustrated in FIGS. 24A and 24B. The valve 1170 is provided in the form of a film, e.g., a disc, as illustrated in FIG. 24A when constructed above the $T_g$ of the polymeric material, thus resulting a normally closed valve. After cooling to below the polymer's $T_g$, the valve 1170 can be deformed to the shape shown in FIG. 24B with an opening formed in the disc. When the valve structure 1170 as seen in FIG. 24B is heated to a temperature above the $T_g$ of the polymer, the valve will revert back to the shape depicted in FIG. 24A, thus occluding the opening formed therein (as seen in FIG. 24B). Alternatively, the valve 1170 can be manufactured as a normally open valve.

Figure 25A:
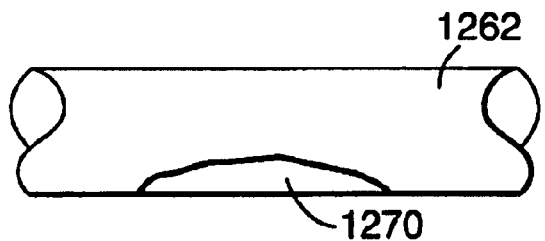
FIGS. 25A & 25B depict an alternative valve structure for use in connection with the devices and methods of the present invention.
Figure 25B:
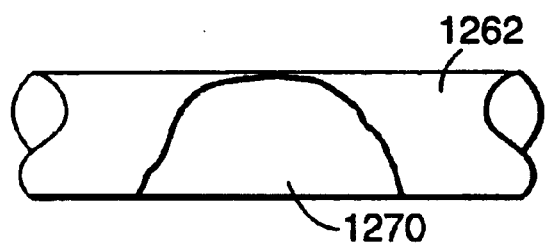

Another alternative valve structure 1270 is depicted in FIGS. 25A and 25B. The depicted valve structure 1270 may be located along a fluid path 1262 (e.g., via or distribution channel). The valve structure 1270 may be provided in the form of material located along the fluid path 1262. When heated above a selected temperature, the material of the valve structure 1270 expands to close the fluid path 1262. The material used in the valve structure 1270 may be, e.g., polymer that expands to form a foamed polymer. The foaming action may be provided, e.g., by using a blowing agent or supercritical carbon dioxide impregnation.

Where a blowing agent is used in the valve structure 1270, it may be impregnated into the polymer. Examples of suitable blowing agents may include, but are not limited to: CELOGEN AZ (available from Uniroyal Corporation, Middlebury, Conn.), EXPANCEL microspheres (Expancel, Sweden), and glycidyl azide based polymers (available from Minnesota Mining and Manufacturing Company, St. Paul, Minn.). When the impregnated polymer is then heated above a selected temperature, the blowing agent generates a gas that causes the polymer to foam and expand and close the valve structure 1270 as depicted in FIG. 25B.

Supercritical foaming may also be used to expand the valve structure 1270. A polymer may be caused to foam by impregnating the polymer with, e.g., carbon dioxide, when the polymer is heated above its glass transition temperature, with the impregnating occurring under high pressure. The carbon dioxide may be applied in liquid form to impregnate the polymeric matrix. The impregnated material can be fabricated into the valve structure, preferably in a compressed form. When heated the carbon dioxide expands, the structure also expands, thereby closing the fluid path 1262.

Although not required, it may be possible to use a foamed shape memory polymeric material to form the valve structure 1270, with the expansion of the foam enhancing the sealing effect of the valve structure 1270 on the fluid path 1262.

In addition, it is possible to use a variant of the structure 1170 depicted in FIG. 24B, wherein the material is shape memory foam prepared by the use of blowing agent or supercritical carbon dioxide gas, which is then fabricated into the structure 1170. The application of heat causes the structure to revert to that of FIG. 24A, with the expansion of the foam enhancing the sealing effect.

Figure 26:
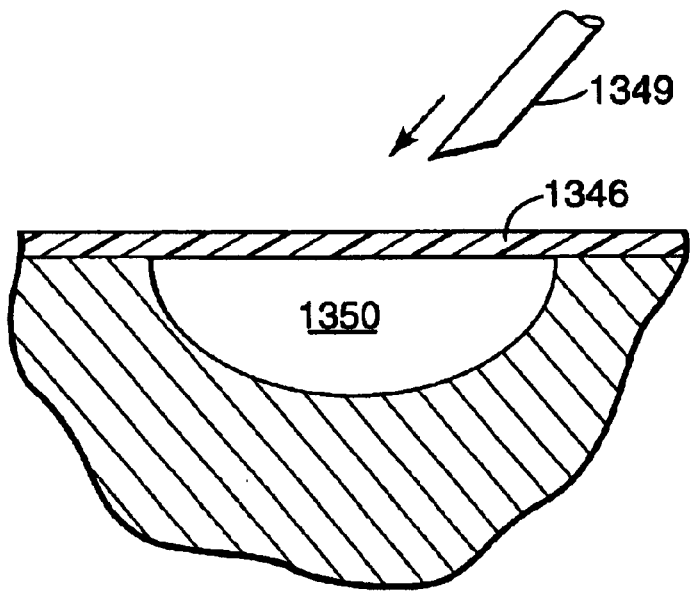
FIG. 26 depicts an alternative seal system for use in connection with the devices and methods of the present invention.

A seal system that exploits the characteristics of shape memory polymeric materials is depicted in FIG. 26. The seal system may be used to provide a resealable access port into, e.g., a process chamber 1350 or other fluid structure on a device of the present invention. The seal system embodiment depicted in FIG. 26 includes an opening 1344 into a process chamber 1350, with the opening being closed by a seal 1346.

The seal 1346 is preferably provided in the form of a film, e.g., a barrier as depicted in FIG. 26, that is constructed above the $T_g$ of the polymeric material, thus resulting a normally closed seal. The seal 1346 can be pierced by a tool 1349 (e.g., a syringe needle) to either deposit material in and/or remove material from the process chamber 1350. The seal 1346 is thus deformed to include an opening formed in the disc. When the seal 1346 is deformed while at a temperature below the $T_g$ of the shape memory polymeric material, that opening can be closed by heating the seal 1346 to a temperature above the $T_g$ of the polymer, thus causing the seal 1346 to revert back to the shape depicted in FIG. 26 and closing the opening formed therein. The piercing and resealing of the seal 1346 may, in some instances be performed two or more times if so desired.

Figure 27:
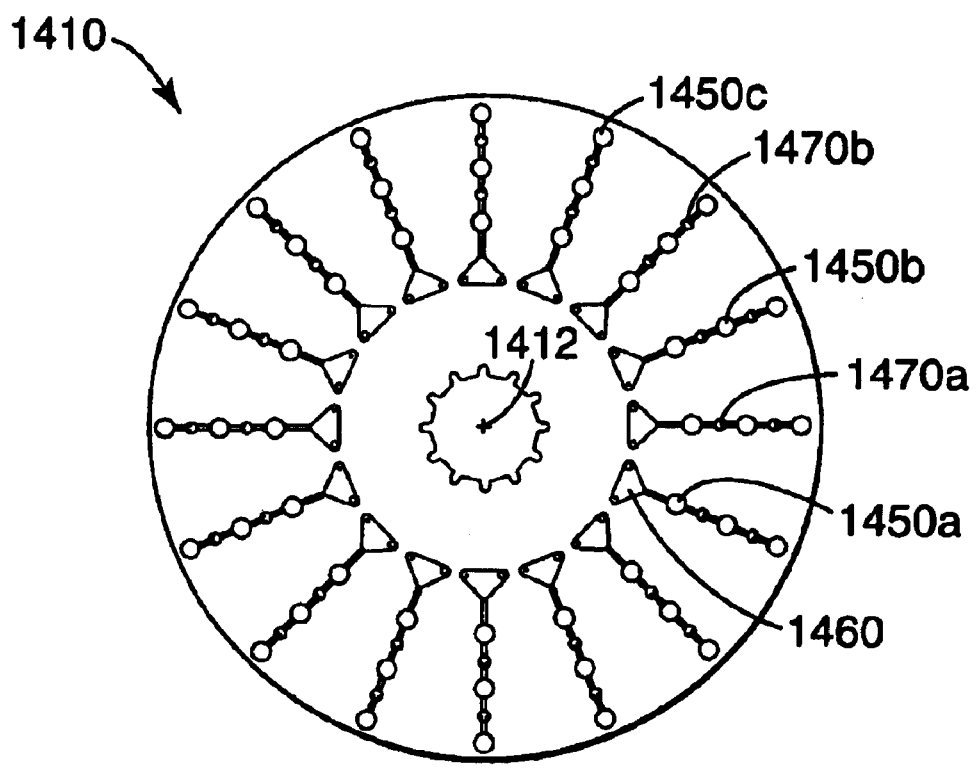
FIG. 27 depicts another sample processing device of the present invention.
Figure 28:
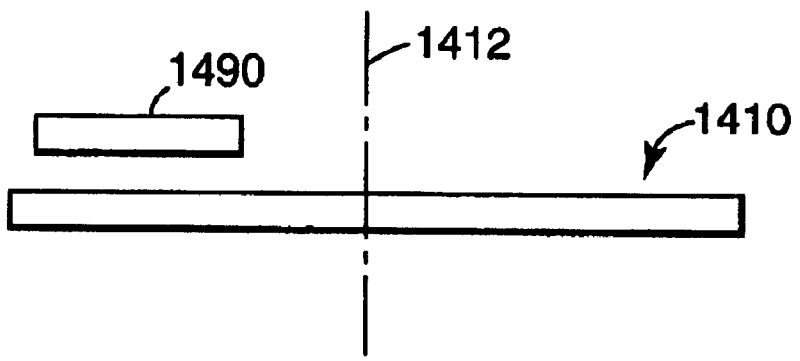
FIG. 28 is a side view of the sample processing device of FIG. 27 with a magnet located proximate the device.

FIGS. 27 and 28 depict another aspect of the sample processing methods and systems of the present invention. This portion of the invention addresses the issue of removing residual reaction materials after, e.g., Sanger cycling. Processes such as Sanger cycling may provide desired reaction products along with residual materials such as unincorporated dye terminators.

When Sanger cycling is performed in the sample processing devices of the present invention, one potential technique for removing the unwanted materials (e.g., dyes) may involve the use of a solid phase material such as paramagnetic particles. One example of suitable paramagnetic particles incorporating dye terminator removal materials is available under the tradename RAPXTRACT from Prolinx Inc., Bothell, Wash. Further examples of these and similar materials (and their methods of use) may be found in International Publication No. WO 01/25490 (titled: REMOVAL OF DYELABELED DIDEOXY TERMINATORS FROM DNA SEQUENCING REACTIONS), and its priority documents (U.S. Patent Application Serial Nos. 60/158,188; 60/164,050; and Ser. No. 09/564,117), as well as in International Publication No. WO 01/25491 (titled: REMOVAL OF DYE-LABELED DIDEOXY TERMINATORS FROM DNA SEQUENCING REACTIONS), and its priority documents (U.S. Patent Application Serial Nos. 60/158,188, 60/164,050; and Ser. No. 09/564,117).

Referring to FIG. 27, one method of using paramagnetic particles in connection with one sample processing device 1410 will be described. After loading the sample material into the loading chambers 1460, the device 1410 is rotated about axis 1412 to move the sample material to the first set of process chambers 1450a. The sample material may be processed in process chambers 1450a by performing, e.g., PCR on the sample material. When processing is completed in the first process chambers 1450a, valves 1470a may be opened and the sample material moved to the second set of process chambers 1450b by rotating the device 1410. A second process may be performed on the sample material in the second process chambers 1450b. In the method described herein, the sample material is Sanger cycled within the second process chambers 1450b to produce Sanger sequencing reaction products within the sample material. After Sanger cycling the sample material can be moved to the output chambers 1450c by opening the valves 1470b and rotating the device 1410.

Before delivery of the Sanger sequencing reaction products to the output chambers 1450c, however, it may be preferred to remove unwanted materials such as unincorporated dye terminators. To do so, paramagnetic particles including, e.g., dye terminator removal material may be introduced into the loading chambers 1460, followed by rotating the device 1410 to move the paramagnetic particles out to the second process chambers 1450b where the unincorporated dye terminators may be captured.

Movement of the paramagnetic particles through the device 1410 may be facilitated by locating a magnet proximate the device 1410. Referring to FIG. 28, a magnet 1490 may be located, e.g., above the device 1410, such that a magnetic field generated by the magnet extends through the process chambers as the device 1410 rotates about the axis 1412. As the paramagnetic particles are moved through the strongest portions of the magnetic field they are moved within the device 1410. The magnetic forces may, therefore, prevent the particles from becoming packed into any distribution channels or other smaller fluid pathways within the device 1410.

In addition, the magnetic forces may also facilitate mixing of the paramagnetic particles within any sample materials in which they are located. For example, it may be preferred to locate the magnet 1490 on the opposite side of the device 1410 from the direction in which gravity pulls the paramagnetic particles. In another variation, two or more magnets may be located on opposite sides of the device 1410 to provide opposing forces on the paramagnetic particles (with the magnets offset around the circumference of the device 1410). In either case, the paramagnetic particles may be subjected to forces pulling in opposite directions intermittently. Additionally, it may be preferred to vary the rotational speed of the device 1410 to further facilitate mixing of the paramagnetic particles in the process chambers.

After the paramagnetic particles have resided in the sample material for a sufficient period of time, they are preferably removed before the sample materials are sequenced. One preferred method of removing the paramagnetic particles is by filtering the sample material during, e.g., moving the sample material from the second process chambers 1450b to the output chambers 1450c. The paramagnetic particles may be filtered using, e.g., filters located between the second process chambers 1450b and the output chambers 1450c. Suitable filters may be in the form of, e.g., the porous plugs 670 described above in connection with FIG. 13. Another alternative filter may be the permeable supports 874 described in connection with FIG. 19. As the device 1410 is rotated about axis, the sample material moves through the filter while the paramagnetic particles are prevented from moving on to the output chamber 1450c.

Rather than moving the paramagnetic particles to the process chambers where they are need by rotating, it may be possible to locate the paramagnetic particles could be dried-down in the process chambers where they can be released when the sample material enters the process chamber. In another alternative, it may be possible to locate the paramagnetic particles in a porous membrane or plug such that the unincorporated dye terminator material can be extracted as the sample material moves through that structure.

Figure 29:
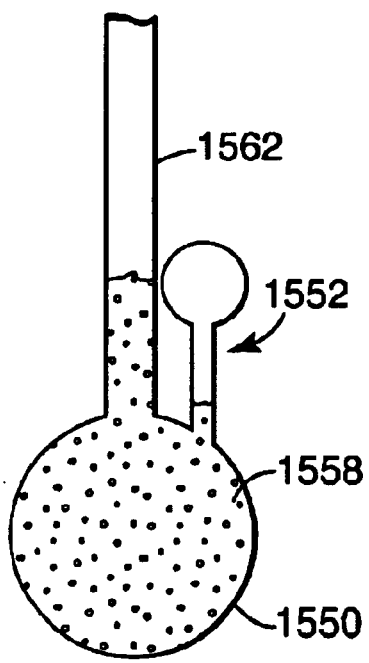
FIGS. 29 & 30 depict an alternative process chamber construction including an expansion chamber to assist with mixing of materials in the process chamber.
Figure 30:
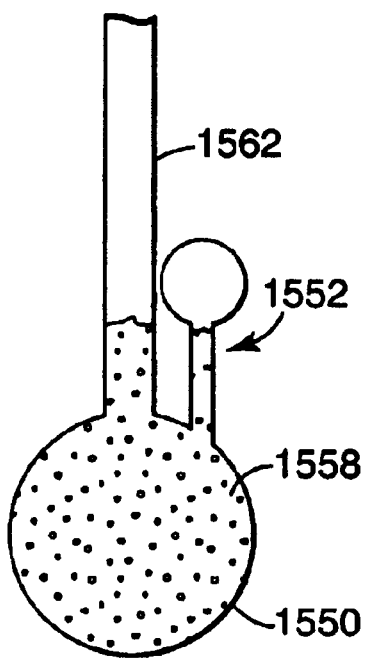

FIGS. 29 & 30 depict a device structure and method that may facilitate mixing of sample material 1558 within a process chamber 1550. Sample material 1558 is delivered to the process chamber 1550 through distribution channel 1562 while rotating the device containing the process chamber 1550. The rotation preferably moves sample material 1558 into the process chamber 1550 by centrifugal force. As discussed above, air or other fluids located within the process chamber 1550 before delivery of the sample material 1558 can be replaced by, e.g., varying the rotational speed of the device.

The process chamber 1550 includes an optional expansion chamber 1552 that cannot be filled with sample material 1558 by rotation of the device containing the process chamber 1550. Filling of the expansion chamber 1552 with sample material 1558 can be prevented, for example, by proper positioning of the expansion chamber 1552 relative to the process chamber 1550. In the depicted embodiment, the expansion chamber 1552 is aligned with the distribution channel 1562 and, as a result, extends from the process chamber 1550 generally back towards the axis of rotation of the device.

Referring to FIG. 30, the sample material 1558 may be forced further into the expansion chamber 1552 as its pressure increases during acceleration of the device and move back out of the expansion chamber 1552 as the pressure decreases when the rotational speed of the device is decreased. By alternately accelerating/decelerating the device, movement of the sample material 1558 into and out of the expansion chamber 1552 can be effected to enhance mixing of the sample material 1558.

Figure 31:
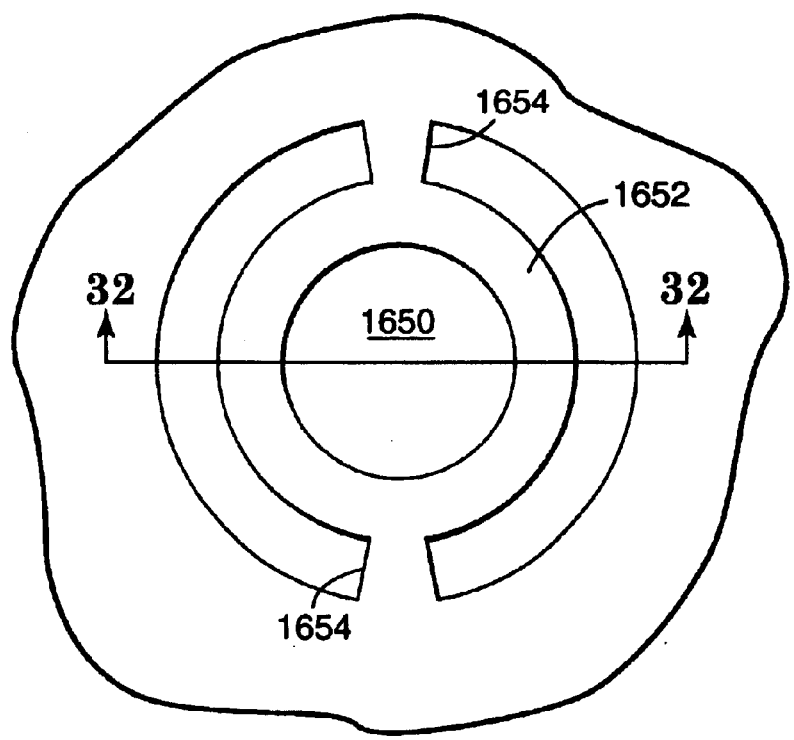
FIGS. 31 & 32 depict another alternative process chamber construction for use in devices according to the present invention.
Figure 32:
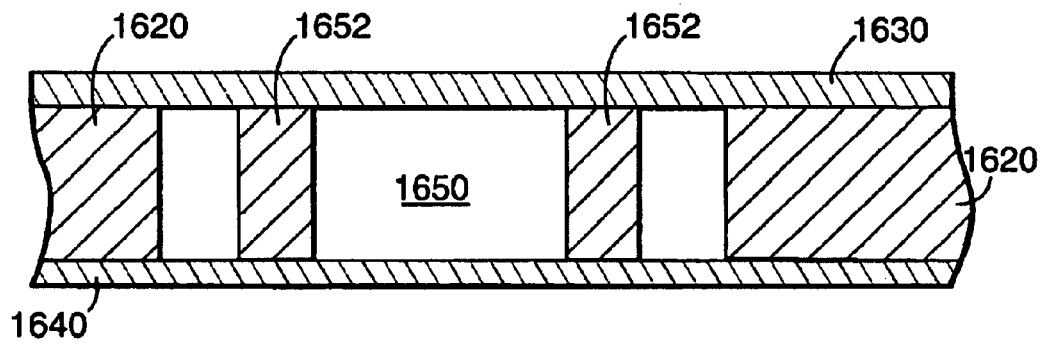

FIGS. 31 & 32 depict another potential feature that may be incorporated into sample processing devices of the present invention. In the figures, thermal isolation of a process chamber 1650 in the device can be enhanced by removing material around the process chamber 1650, with the process chamber 1650 being defined by a ring 1652 connected to the surrounding body 1654 by one or more struts 1656. Essentially, the process chamber 1650 is surrounded by one or more voids. Channels to deliver sample materials to the process chamber 1650 or remove sample materials from the process chamber 1650 can be located along the support struts 1654. Thermal isolation is improved by removing material around the ring 1652 that could serve as a heat sink, drawing thermal energy away from the process chamber 1650 during heating, or supplying stored thermal energy to the process chamber when cooling is desired.

As depicted, the cover layers 1630 and 1640 provided on both sides of the core 1620 may extend over the voids formed around the process chamber 1650, thereby providing a contained volume of air or other insulating material. Alternatively, one or both of the cover layers 1630 and 1640 may be removed from around the ring 1652.

Figure 33:
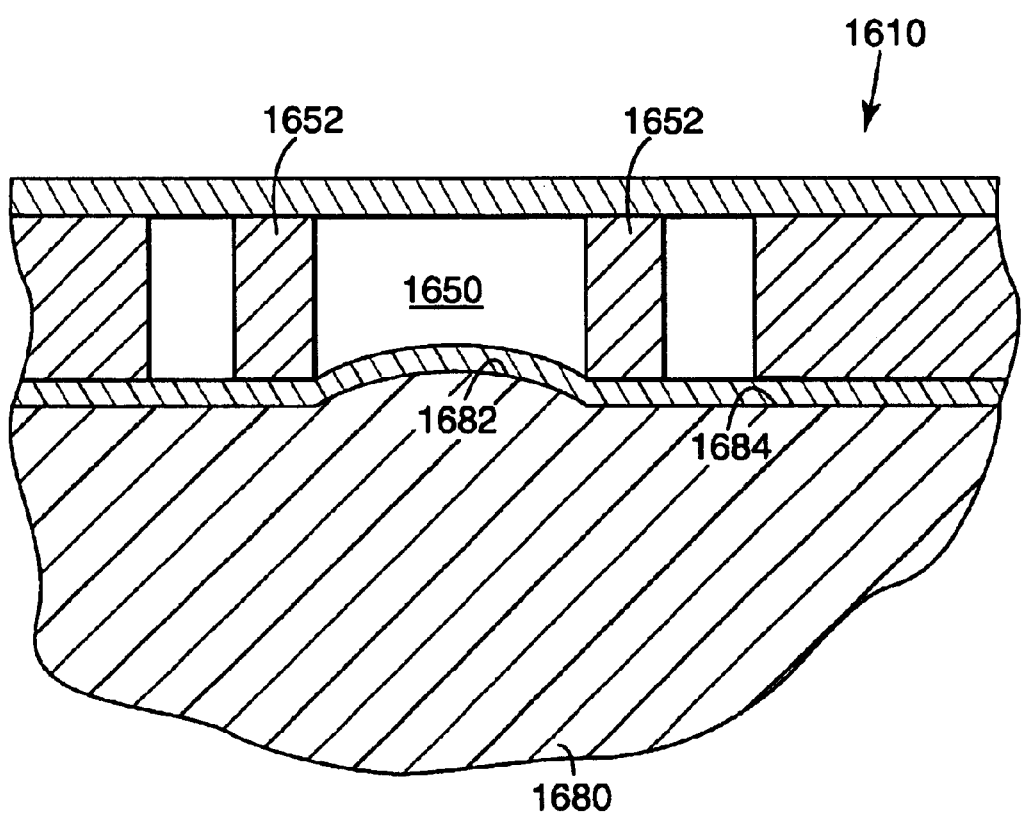
FIG. 33 depicts the process chamber construction of FIGS. 31 & 32 in conjunction with a mating base plate protrusion for use in connection with the present invention.

In addition to the enhanced thermal isolation of the suspended process chambers 1650, the suspended construction may offer improved compliance of the process chamber 1650 to a base plate or other structure on which the device may be placed. The improved compliance may be provided by the struts Turning to FIG. 33, another optional feature of devices according to the present invention is depicted. The device of FIGS. 31 & 32 is depicted as located on a base plate 1680 that includes raised protrusions 1682 that are located beneath the process chambers 1650. It is preferred that the protrusions 1682 extend above the surrounding surface 1684 of the base plate 1680.

The protrusions 1682 may enhance thermal transfer between the process chamber 1650 and base plate 1680 in a number of ways. When the protrusions 1682 extend at least partially into the process chambers 1650, they increase the surface area of the chamber 1650 that is exposed to the heated base plate 1680. In addition, by affirmatively engaging the process chambers 1650, the protrusions 1682 may reduce or eliminate any air gaps between the process chambers 1650 and the base plate 1680 in the area of the process chambers 1650. Such air gaps may insulate the process chambers 1650 from the base plate 1680, thereby degrading thermal transfer.

It may be preferred that the portions of the process chambers 1650 in contact with the protrusions 1680 exhibit sufficient compliance to deform in response to placement on the base plate 1680. For example, the cover layer 1640 may preferably include a deformable metallic foil. In addition, it may be preferred to provide the process chambers 1650 in suspended rings 1652 as described above with respect to FIGS. 31 & 32 (which may offer improved compliance).

Further, it may be desirable to supply a force on the device 1610 in which process chambers 1650 are located to urge the device 1610 and base plate 1680 towards each other. In some embodiments, the force may be provided by a platen urging the device 1610 against the base plate 1680. In other embodiments, the device 1610 may be drawn towards the base plate 1680 by, e.g., a spindle that extends through a central opening in the device 1610 and draws the device 1610 towards base plate 1680. Other structures for providing a force urging the device 1610 and base plate 1680 together will be known to those skilled in the art.

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A method of conducting a thermal cycling process comprising:

providing a device comprising a plurality of process chambers, each process chamber of the plurality of process chambers defining a volume for containing sample material;

providing a base plate comprising a top surface, a bottom surface, and a thermal structure;

locating a first major surface of the device in contact with the top surface of the base plate, wherein at least some process chambers of the plurality of process chambers are in thermal communication with the thermal structure when the device is in contact with the top surface of the base plate;

providing sample material in the plurality of process chambers; and controlling the temperature of the thermal structure by directing electromagnetic energy at the bottom surface of the base plate while rotating the base plate and the device about the axis of rotation, whereby the temperature of the sample material is controlled.

2. The method of claim 1, wherein the thermal structure comprises at least one substantially continuous circular ring in the base plate.

3. The method of claim 1, wherein the thermal structure comprises a plurality of independent thermal structures.

4. The method of claim 1, wherein the base plate comprises a plurality of independent thermal structures, and wherein the method further comprises directing electromagnetic energy at different thermal elements of the plurality of independent thermal elements at different times.

5. The method of claim 1, further comprising directing electromagnetic energy into the plurality of process chambers while directing electromagnetic energy at the bottom surface of the base plate.

6. The method of claim 1, further comprising directing electromagnetic energy into the plurality of process chambers while directing electromagnetic energy at the bottom surface of the base plate, and wherein the device further comprises electromagnetic energy receptive materials proximate the plurality of process chambers, wherein the electromagnetic energy receptive materials convert the electromagnetic energy directed into the plurality of process chambers into thermal energy.

7. The method of claim 1, wherein the device further comprises baffle structures on a second major surface of the device.

8. The method of claim 1, wherein the device further comprises directional baffle structures on a second major surface of the device, and further wherein the directional baffle structures increase the rate of thermal energy transfer out of the plurality of process chambers when rotating the device in one direction relative to the rate of thermal energy transfer out of the plurality of process chambers when rotating the device in an opposite direction.

9. The method of claim 1, wherein the device further comprises a control pattern, the control pattern comprising at least one indicator associated with each of the process chambers, the method further comprising:
 detecting the control pattern while rotating the base plate and the devices; and
 controlling the electromagnetic energy directed at the bottom surface of the base plate based on detecting the control pattern.

10. The method of claim 1, wherein the thermal structure further comprises at least one thermoelectric module, and wherein the method further comprises controlling the temperature of the at least one thermoelectric module while rotating the base plate and the device.

11. The method of claim 1, wherein the thermal structure further comprises at least one thermoelectric module, and wherein the method further comprises controlling the temperature of the at least one thermoelectric module and directing electromagnetic energy at the bottom surface of the base plate while rotating the base plate and the device.

12. The method of claim 1, wherein the thermal structure further comprises at least one thermoelectric module;
 wherein the method further comprises controlling the temperature of the at least one thermoelectric module and directing electromagnetic energy at the bottom surface of the base plate while rotating the base plate and the device;
 and wherein the method further comprises delivering electromagnetic energy to the process chambers while directing electromagnetic energy at a bottom surface of the thermal structure, controlling the temperature of the at least one thermoelectric module, and rotating the base plate and the device.

13. The method of claim 1, wherein the top surface of the base plate comprises a plurality of raised protrusions extending above the top surface surrounding each raised protrusion of the plurality of protrusions, wherein each raised protrusion is aligned with one process chamber of the plurality of process chambers.

14. The method of claim 1, further comprising monitoring the temperature of the sample material while rotating the device.

15. The method of claim 1, further comprising monitoring the temperature of the thermal structure while rotating the device.

16. The method of claim 1, wherein controlling the temperature of the thermal structure comprises sequentially increasing and decreasing the temperature of the thermal structure through at least two cycles of increasing and decreasing temperature.

17. The method of claim 1, wherein at least one process chamber of the plurality of process chambers comprises a cover layer comprising an inner surface facing an interior of the at least one process chamber, an opening formed through the cover layer, and a seal attached to the inner surface of the cover layer, whereby the opening formed through the cover layer is sealed; wherein the method further comprises forcing the seal away from the inner surface of the cover layer to access to the interior of the at least one process chamber.

18. The method of claim 1, wherein at least one process chamber of the plurality of process chambers comprises a seal comprising shape memory polymer, and wherein the method further comprises piercing the seal to access the interior of the at least one process chamber.

19. The method of claim 18, further comprising heating the shape memory polymer to reseal the cover layer after the piercing.

20. The method of claim 1, wherein each process chamber of the plurality of process chambers comprises an expansion chamber, and wherein the method further comprises mixing the sample material in each of the process chambers by rotating the device about the axis of rotation to move sample material into and out of the expansion chamber.

21. A method of conducting a thermal cycling process comprising:
 providing a device comprising a plurality of process chambers, each process chamber of the plurality of process chambers defining a volume for containing sample material;
 providing a base plate comprising a top surface, a bottom surface, and a thermal structure that comprises at least one thermoelectric module;
 locating a first major surface of the device in contact with the top surface of the base plate, wherein the plurality of process chambers are in thermal communication with the thermal structure when the device is in contact with the top surface of the base plate;
 providing sample material in the plurality of process chambers; and
 controlling the temperature of the thermal structure by controlling the temperature of the at least one thermoelectric module while rotating the base plate and the device about the axis of rotation, wherein the temperature of the sample material is controlled.

22. The method of claim 21, wherein the thermal structure comprises at least one substantially continuous circular ring in the base plate.

23. The method of claim 21, wherein the thermal structure comprises a plurality of independent thermal structures, and farther wherein each thermal element comprises at least one of the at least one thermoelectric modules.

24. The method of claim 21, further comprising directing electromagnetic energy into the plurality of process chambers while controlling the temperature of the at least one thermoelectric module of the thermal structure.

25. The method of claim 21, further comprising directing electromagnetic energy into the plurality of process chambers while controlling the temperature of the at least one thermoelectric module of the thermal structure, and wherein the device further comprises electromagnetic energy receptive materials proximate the plurality of process chambers, wherein the electromagnetic energy receptive materials convert the electromagnetic energy directed into the plurality of process chambers into the mal energy.

26. The method of claim 21, wherein the device further comprises baffle structures on a second major surface of the device.

27. The method of claim 21, wherein the device further comprises directional baffle structures on a second major surface of the device, and further wherein the directional baffle structures increase the rate of thermal energy transfer out of the plurality of process chambers when rotating the device in one direction relative to the rate of thermal energy transfer out of the plurality of process chambers when rotating the device in an opposite direction.

28. The method of claim 21, wherein the top surface of the base plate comprises a plurality of raised protrusions extending above the top surface surrounding each raised protrusion of the plurality of protrusions, wherein each raised protrusion is aligned with one process chamber of the plurality of process chambers.

29. The method of claim 21, further comprising monitoring the temperature of the sample material while rotating the device.

30. The method of claim 21, wherein controlling the temperature of the thermal structure comprises sequentially increasing and decreasing the temperature of the thermal structure through at least two cycles of increasing and decreasing temperature.

31. The method of claim 21, wherein at least one process chamber of the plurality of process chambers comprises a cover layer comprising an inner surface facing an interior of the at least one process chamber, an opening formed through the cover layer, and a seal attached to the inner surface of the cover layer, whereby the opening fanned through the cover layer is sealed; wherein the method further comprises forcing the seal away from the inner surface of the cover layer to access to the interior of the at least one process chamber.

32. The method of claim 21, wherein at least one process chamber of the plurality of process chambers comprises a seal comprising shape memory polymer, and wherein the method further comprises piercing the seal to access the interior of the at least one process chamber.

33. The method of claim 32, further comprising heating the shape memory polymer to reseal the cover layer after the piercing.

34. The method of claim 21, wherein each process chamber of the plurality of process chambers comprises an expansion chamber, and wherein the method further comprises mixing the sample material in each of the process chambers by rotating the device about the axis of rotation to move sample material into and out of the expansion chamber.

35. A method of conducting a thermal cycling process comprising:
providing a device comprising a plurality of process chambers, each process chamber of the plurality of process chambers defining a volume for containing sample material;
providing sample material in the plurality of process chambers;
directing electromagnetic energy into the plurality of process chambers to raise the temperature of the sample material in the plurality of process chambers; and
rotating the device about an axis of rotation while directing electromagnetic energy into the plurality of process chambers, wherein the temperature of the sample material in the plurality of process chambers is controlled as the device rotates about the axis of rotation.

36. The method of claim 35, wherein the device further comprises electromagnetic energy receptive materials proximate the plurality of process chambers, wherein the electromagnetic energy receptive materials convert the electromagnetic energy directed into the plurality of process chambers into thermal energy.

37. The method of claim 35, wherein the device further comprises baffle structures on a second major surface of the device.

38. The method of claim 35, wherein the device further comprises directional baffle structures on a second major surface of the device, and further wherein the directional baffle structures increase the rate of thermal energy transfer out of the plurality of process chambers when rotating the device in one direction relative to the rate of thermal energy transfer out of the plurality of process chambers when rotating the device in an opposite direction.

39. The method of claim 35, wherein the device further comprises a control pattern, the control pattern comprising at least one indicator associated with each of the process chambers, the method further comprising:
detecting the control pattern while rotating the base plate and the devices; and
controlling the electromagnetic energy directed into the plurality of process chambers based on detecting the control pattern.

40. The method of claim 35, further comprising monitoring the temperature of the sample material while rotating the device.

41. The method of claim 35, further comprising sequentially increasing and decreasing the temperature of the sample material in the plurality of process chambers through at least two cycles of increasing and decreasing temperature.

42. The method of claim 35, wherein at least one process chamber of the plurality of process chambers comprises a cover layer comprising an inner surface facing an interior of the at least one process chamber, an opening fanned through the cover layer, and a seal attached to the inner surface of the cover layer, whereby the opening fanned through the cover layer is sealed; wherein the method further comprises forcing the seal away from the inner surface of the cover layer to access to the interior of the at least one process chamber.

43. The method of claim 35, wherein at least one process chamber of the plurality of process chambers comprises a seal comprising shape memory polymer, and wherein the method further comprises piercing the seal to access the interior of the at least one process chamber.

44. The method of claim 35, further comprising heating the shape memory polymer to reseal the cover layer alter the piercing.

45. The method of claim 35, wherein each process chamber of the plurality of process chambers comprises an expansion chamber, and wherein the method further comprises mixing the sample material in each of the process chambers by rotating the device about the axis of rotation to move sample material into and out of the expansion chamber.

46. A method of processing sample material comprising:
providing a device comprising at least one process chamber array that comprises a loading chamber and a first process chamber;
providing sample material in the at least one process chamber array, the sample material being provided in the loading chamber of the at least one process chamber array;
moving the sample material from the loading chamber to the first process chamber of the at least one process chamber array by rotating the device the device about an axis of rotation;
providing a base plate comprising a top surface, a bottom surface, and a thermal structure;
locating a first major surface of the device in contact with the top surface of the base plate, wherein the first process chamber of the at least one process chamber array is in thermal communication with the thermal structure when the device is in contact with the top surface of the base plate; and controlling the temperature of the thermal structure by directing electromagnetic energy at the bottom surface of the base plate while rotating the base plate and the device about the axis of rotation, whereby the temperature of the sample material is controlled.

47. The method of claim 46, wherein the thermal structure comprises at least one substantially continuous circular ring in the base plate.

48. The method of claim 46, wherein the thermal structure comprises a plurality of independent thermal structures.

49. The method of claim 46, wherein the base plate comprises a plurality of independent thermal structures, and wherein the method further comprises directing electromagnetic energy at different thermal elements of the plurality of independent thermal elements at different times.

50. The method of claim 46, further comprising delivering electromagnetic energy into the first process chamber of the at least one process chamber array while directing electromagnetic energy at the bottom surface of the base plate.

51. The method of claim 46, further comprising directing electromagnetic energy into the first process chamber of the at least one process chamber array while directing electromagnetic energy at the bottom surface of the base plate, and wherein the device further comprises electromagnetic energy receptive materials proximate the first process chamber of the at least one process chamber array, wherein the electromagnetic energy receptive materials convert the electromagnetic energy directed into the first process chamber of the at least one process chamber array into thermal energy.

52. The method of claim 46, wherein the device further comprises baffle structures on a second major surface of the device.

53. The method of claim 46, wherein the device further comprises directional baffle structures on a second major surface of the device, and further wherein the directional baffle structures increase the rate of thermal energy transfer out of the first process chamber of the at least one process chamber array when rotating the device in one direction relative to the rate of thermal energy transfer out of the first process chamber of the at least one process chamber array when rotating the device in an opposite direction.

54. The method of claim 46, wherein the device further comprises a control pattern, the control pattern comprising at least one indicator associated with the first process chamber of the at least one process chamber array, the method further comprising:

detecting the control pattern while rotating the base plate and the devices; and controlling the electromagnetic energy directed at the bottom surface of the base plate based on detecting the control pattern.

55. The method of claim 46, wherein the thermal structure further comprises at least one thermoelectric module, and wherein the method further comprises controlling the temperature of the at least one thermoelectric module while rotating the base plate and the device.

56. The method of claim 46, wherein the thermal structure further comprises at least one thermoelectric module, and wherein the method further comprises controlling the temperature of the at least one thermoelectric module and directing electromagnetic energy at the bottom surface of the base plate while rotating the base plate and the device.

57. The method of claim 46, wherein the thermal structure further comprises at least one thermoelectric module;

wherein the method further comprises controlling the temperature of the at least one thermoelectric module and directing electromagnetic energy at the bottom surface of the base plate while rotating the base plate and the device;

and wherein the method further comprises delivering electromagnetic energy to the first process chamber of the at least one process chamber array while directing electromagnetic energy at a bottom surface of the thermal structure, controlling the temperature of the at least one thermoelectric module, and rotating the base plate and the device.

58. The method of claim 46, wherein the top surface of the base plate comprises a plurality of raised protrusions extending above the top surface surrounding each raised protrusion of the plurality of protrusions, wherein each raised protrusion is aligned with one first process chamber of each process chamber array of the plurality of process chamber arrays.

59. The method of claim 46, further comprising monitoring the temperature of the sample material while rotating the device.

60. The method of claim 46, further comprising monitoring the temperature of the thermal structure while rotating the device.

61. The method of claim 46, wherein the rotating during moving the sample material comprises at least two acceleration/deceleration cycles.

62. The method of claim 46, wherein the at least one process chamber array comprises an unvented process chamber array.

63. The method of claim 46, further comprising filtering the sample material while moving the sample material from the loading chamber to the first process chamber in the at least one process chamber array.

64. The method of claim 46, wherein controlling the temperature of the thermal structure comprises sequentially increasing and decreasing the temperature of the thermal structure through at least two cycles of increasing and decreasing temperature.

65. The method of claim 46, wherein the at least one process chamber array comprises a second process chamber;

and wherein the second process chamber of the at least one process chamber array is in thermal communication with the thermal structure when the device is in contact with the top surface of the base plate;

and wherein the method further comprises:

moving the sample material from the first process chamber of the at least one process chamber array to the second process chamber in the at least one process chamber array by rotating the device;

heating the thermal structure by directing electromagnetic energy at the bottom surface of the base plate after moving the sample material to the second process chamber of the at least one process chamber array; and rotating the base plate and the device about the axis of rotation while heating the thermal structure, whereby the temperature of the sample material in the second process chamber of the at least one process chamber array is controlled.

66. The method of claim 65, wherein the at least one process chamber array comprises a valve located between the first process chamber and the second process chamber, the valve comprising an impermeable barrier, the method further comprising placing the first process chamber of the at least one process chamber array in fluid communication with the second process chamber of the at least one process chamber array by forming a void in the impermeable barrier of the valve.

67. The method of claim 65, wherein the at least one process chamber array comprises a valve located between the first process chamber and the second process chamber, the valve comprising shape memory polymer, the method further comprising placing the first process chamber of the at least one process chamber array in fluid communication with the second process chamber of the at least one process chamber array by opening the valve.

68. The method of claim 65, further comprising filtering the sample material while moving the sample material from the first process chamber to the second process chamber in the at least one process chamber array.

69. The method of claim 65, wherein the at least one process chamber array further comprises an output chamber, and wherein the method further comprises moving the sample material from the second process chamber of the at least one process chamber array to the output chamber of the at least one process chamber array by rotating the device.

70. The method of claim 69, further comprising filtering the sample material while moving the sample material from the second process chamber to the output chamber in the at least one process chamber array.

71. A method of conducting a thermal cycling process comprising:
   providing a device comprising a plurality of process chamber arrays, each process chamber array of the plurality of process chamber arrays comprising a loading chamber and a first process chamber;
   providing a base plate comprising a top surface, a bottom surface, and a thermal structure that comprises at least one thermoelectric module;
   locating a first major surface of the device in contact with the top surface of the base plate, wherein the first process chamber of at least one process chamber array of the plurality of process chamber arrays is in thermal communication with the thermal structure when the device is in contact with the top surface of the base plate;
   providing sample material in at least one process chamber array of the plurality of process chamber arrays, the sample material being provided in the loading chamber of the at least one process chamber array;
   moving the sample material from the loading chamber to the first process chamber of the at least one process chamber array by rotating the device about an axis of rotation; and
   controlling the temperature of the thermal structure by controlling the temperature of the at least one thermoelectric module while rotating the base plate and the device about the axis of rotation, wherein the temperature of the sample material is controlled.

72. The method of claim 71, wherein the thermal structure comprises at least one substantially continuous circular ring in the base plate.

73. The method of claim 71, wherein the thermal structure comprises a plurality of independent thermal structures, and further wherein each thermal element comprises at least one of the at least one thermoelectric modules.

74. The method of claim 71, further comprising directing electromagnetic energy into the first process chamber of the at least one process chamber array while controlling the temperature of the at least one thermoelectric module of the thermal structure.

75. The method of claim 71, further comprising directing electromagnetic energy into the first process chamber of the at least one process chamber array while controlling the temperature of the at least one thermoelectric module of the thermal structure, and wherein the device further comprises electromagnetic energy receptive materials proximate the first process chamber of the at least one process chamber array, wherein the electromagnetic energy receptive materials convert the electromagnetic energy directed into the first process chamber of the at least one process chamber array into thermal energy.

76. The method of claim 71, wherein the device further comprises baffle structures on a second major surface of the device.

77. The method of claim 71, wherein the device further comprises directional baffle structures on a second major surface of the device, and further wherein the directional baffle structures increase the rate of thermal energy transfer out of the plurality of process chambers when rotating the device in one direction relative to the rate of thermal energy transfer out of the plurality of process chambers when rotating the device in an opposite direction.

78. The method of claim 71, wherein the top surface of the base plate comprises a plurality of raised protrusions extending above the top surface surrounding each raised protrusion of the plurality of protrusions, wherein each raised protrusion is aligned with one first process chamber of each process chamber array of the plurality of process chamber arrays.

79. The method of claim 71, further comprising monitoring the temperature of the sample material while rotating the device.

80. The method of claim 71, wherein the rotating during moving the sample material comprises at least two acceleration/deceleration cycles.

81. The method of claim 71, further comprising filtering the sample material while moving the sample material from the loading chamber to the first process chamber in the at least one process chamber array.

82. The method of claim 71, wherein controlling the temperature of the thermal structure comprises sequentially increasing and decreasing the temperature of the thermal structure through at least two cycles of increasing and decreasing temperature.

83. The method of claim 71, wherein each process chamber array of the plurality of process chamber arrays comprises a second process chamber;
   and wherein the second process chamber of the at least one process chamber array is in thermal communication with the thermal structure when the device is in contact with the top surface of the base plate;
   and wherein the method further comprises:
      moving the sample material from the first process chamber of the at least one process chamber array to the second process chamber in the at least one process chamber array by rotating the device;
      controlling the temperature of the at least one thermoelectric module of the thermal structure after moving the sample material to the second process chamber of the at least one process chamber array; and
      rotating the base plate and the device about the axis of rotation while controlling the temperature of the at least one thermoelectric module, whereby the temperature of the sample material in the second process chamber of the at least one process chamber array is controlled.

84. The method of claim 83, wherein each process chamber array of the plurality of process chamber arrays comprises a valve located between the first process chamber and the second process chamber, the valve comprising an impermeable barrier, the method further comprising placing the first process chamber of the at least one process chamber array in fluid communication with the second process chamber of the at least one process chamber array by forming a void in the impermeable barrier of the valve.

85. The method of claim 84, wherein the valve further comprises a permeable support member proximate the impermeable barrier.

86. The method of claim 83, wherein each process chamber array of the plurality of process chamber arrays comprises a valve located between the first process chamber and the second process chamber, the valve comprising shape memory polymer, the method further comprising placing the first process chamber of the at least one process chamber array in fluid communication with the second process chamber of the at least one process chamber array by opening the valve.

87. The method of claim 83, further comprising filtering the sample material while moving the sample material from the first process chamber to the second process chamber in the at least one process chamber array.

88. The method of claim 83, wherein each process chamber array of the plurality of process chamber arrays further comprises an output chamber, and wherein the method further comprises moving the sample material from the second process chamber of the at least one process chamber array to the output chamber of the at least one process chamber array by rotating the device.

89. The method of claim 71, further comprising filtering the sample material while moving the sample material from the second process chamber to the output chamber in the at least one process chamber array.

90. A method of processing sample material comprising:
providing a device comprising a plurality of process chamber arrays, each process chamber array of the plurality of process chamber arrays comprising a loading chamber and a first process chamber;
providing sample material in at least one process chamber array of the plurality of process chamber arrays, the sample material being provided in the loading chamber of the at least one process chamber array;
moving the sample material from the loading chamber to the first process chamber of the at least one process chamber array by rotating the device about an axis of rotation;
directing electromagnetic energy into the first process chamber of the at least one process chamber array to raise the temperature of the sample material in the first process chamber of the at least one process chamber array; and
rotating the device about an axis of rotation while directing electromagnetic energy into the first process chamber of the at least one process chamber array, wherein the temperature of the sample material in the first process chamber of the at least one process chamber array is controlled as the device rotates about the axis of rotation.

91. The method of claim 90, wherein the device further comprises electromagnetic energy receptive materials proximate the first process chamber of the at least one process chamber array, wherein the electromagnetic energy receptive materials convert the electromagnetic energy directed into the first process chamber of the at least one process chamber array into thermal energy.

92. The method of claim 90, wherein the device further comprises baffle structures on a second major surface of the device.

93. The method of claim 90, wherein the device further comprises directional baffle structures on a second major surface of the device, and further wherein the directional baffle structures increase the rate of thermal energy transfer out of the plurality of process chambers when rotating the device in one direction relative to the rate of thermal energy transfer out of the plurality of process chambers when rotating the device in an opposite direction.

94. The method of claim 90, wherein the device further comprises a control pattern, the control pattern comprising at least one indicator associated with the first process chamber of the at least one process chamber array, the method further comprising:
detecting the control pattern while rotating the base plate and the devices; and
controlling the electromagnetic energy directed into the first process chamber of the at least one process chamber array based on detecting the control pattern.

95. The method of claim 90, further comprising monitoring the temperature of the sample material while rotating the device.

96. The method of claim 90, wherein the rotating during moving the sample material comprises at least two acceleration/deceleration cycles.

97. The method of claim 90, further comprising sequentially increasing and decreasing the temperature of the sample material in the first chamber of the at least one process chamber array through at least two cycles of increasing and decreasing temperature.

98. The method of claim 90, wherein each process chamber array of the plurality of process chamber arrays comprises a second process chamber; and wherein the method further comprises:
moving the sample material from the first process chamber of the at least one process chamber array to the second process chamber in the at least one process chamber array by rotating the device;
directing electromagnetic energy into the second process chamber of the at least one process chamber may after moving the sample material to the second process chamber of the at least one process chamber array to raise the temperature of the sample material in the second process chamber of the at least one process chamber array; and
rotating the device about an axis of rotation while directing electromagnetic energy into the second process chamber of the at least one process chamber away, wherein the temperature of the sample material in the second process chamber of the at least one process chamber array is controlled as the device rotates about the axis of rotation.

99. The method of claim 98, wherein each process chamber array of the plurality of process chamber arrays comprises a valve located between the first process chamber and the second process chamber, the valve comprising an impermeable barrier, the method further comprising placing the first process chamber of the at least one process chamber array in fluid communication with the second process chamber of the at least one process chamber array by forming a void in the impermeable barrier of the valve.

100. The method of claim 99, wherein the valve further comprises a permeable support member proximate the impermeable barrier.

101. The method of claim 98, wherein each process chamber array of the plurality of process chamber arrays comprises a valve located between the first process chamber and the second process chamber, the valve comprising shape memory polymer, the method further comprising placing the first process chamber of the at least one process chamber array iii fluid communication with the second process chamber of the at least one process chamber array by opening the valve.

102. The method of claim 98, further comprising filtering the sample material while moving the sample material from the first process chamber to the second process chamber in the at least one process chamber array.

103. The method of claim 98, wherein each process chamber array of the plurality of process chamber arrays further comprises an output chamber, and wherein the method further comprises moving the sample material from the second process chamber of the at least one process chamber array to the output chamber of the at least one process chamber array by rotating the device.

104. The method of claim 103, further comprising filtering the sample material while moving the sample material from the second process chamber to the output chamber in the at least one process chamber array.

105. A device for processing sample material, the device comprising:
    a substrate comprising first and second major surfaces;
    a plurality of process chambers in the device, each of the process chambers defining a volume for containing a sample; and
    a plurality of valves with at least one of the valves located between selected pairs of the process chambers, each valve comprising an impermeable barrier, wherein the impermeable barrier of each of the valves separates the selected pairs of process chambers, and wherein each of the valves comprises a permeable support proximate the impermeable barrier.

106. The device of claim 105, wherein the permeable support comprises a porous disc coextensive with the impermeable barrier.

107. A device for processing sample material, the device comprising:
    a substrate comprising first and second major surfaces;
    a plurality of process chambers in the device, each of the process chambers defining a volume for containing a sample; and
    a plurality of valves with at least one of the plurality of valves located between selected pairs of the process chambers, each valve comprising shape memory polymer.

108. The device of claim 107, wherein at least one of the plurality of valves is normally open.

109. The device of claim 107, wherein at least one of the plurality of valves is normally closed.

110. A device for processing sample material, the device comprising:
    a substrate comprising first and second major surfaces;
    a plurality of process chambers in the device, each of the process chambers defining a volume for containing a sample;
    a seal defining the volume of at least some of the process chambers, wherein the seal comprises shape memory polymer.

111. A device for processing sample material, the device comprising:
    a substrate comprising first and second major surfaces;
    a plurality of process chambers in the device, each of the process chambers defining a volume for containing a sample; and
    a control pattern on the device, the control pattern comprising at least one indicator associated with each of the plurality of process chambers, each of the indicators having at least one characteristic indicative of electromagnetic energy to be delivered to each process chamber associated with that indicator, whereby the delivery of the electromagnetic energy to selected process chambers can be controlled.

112. A sample processing system comprising:
    a rotating base plate;
    at least one thermal structure attached to the base plate, the at least one thermal structure comprising a top surface and a bottom surface; and
    at least one thermoelectric module in thermal communication with the thermal structure, the at least one thermoelectric module arranged to control the temperature of the thermal structure while the base plate is rotating, and further comprising an electromagnetic energy source arranged to direct electromagnetic energy towards the top surface of the at least one thermal structure.

* * * * *

UNITED STATES PATENT AND TRADEMARK OFFICE
CERTIFICATE OF CORRECTION

PATENT NO. : 6,734,401 B2
DATED : May 11, 2004
INVENTOR(S) : Bedingham, William

It is certified that error appears in the above-identified patent and that said Letters Patent is hereby corrected as shown below:

Title page,
Item [60], Related U.S. Application Data, delete "60/237,072" and insert -- 60/237,151 --, therefor.

Column 1,
Line 11, delete "60/237,072" and insert -- 60/237,151 --, therefor.

Column 34,
Line 14, delete "97b" and insert -- 972b --, therefor.

Column 42,
Line 48, delete "farther" and insert -- further --, therefor.
Line 62, delete "the mal" and insert -- thermal --, therefor.

Column 43,
Line 25, delete "fanned" and insert -- formed --, therefor.

Column 44,
Lines 28 and 30, delete "fanned" and insert -- formed --, therefor.
Line 40, delete "alter" and insert -- after --, therefor.

Column 50,
Line 40, delete "may" and insert -- array --, therefor.
Line 48, delete "away" and insert -- array --, therefor.

UNITED STATES PATENT AND TRADEMARK OFFICE
CERTIFICATE OF CORRECTION

PATENT NO.    : 6,734,401 B2
DATED         : May 11, 2004
INVENTOR(S)   : Bedingham, William It is certified that error appears in the above-identified patent and that said Letters Patent is hereby corrected as shown below:

<u>Column 51,</u>
Line 4, delete "iii" and insert -- in --, therefor.

Signed and Sealed this

Twenty-fifth Day of January, 2005

JON W. DUDAS
*Director of the United States Patent and Trademark Office*